(12) United States Patent
Helms et al.

(10) Patent No.: US 11,565,995 B2
(45) Date of Patent: Jan. 31, 2023

(54) METHODS OF FORMING IMINES, IMINE-RELATED AND IMINE-DERIVED COMPOUNDS USING GREEN SOLVENTS

(71) Applicant: Research Foundation for the State University of New York, Albany, NY (US)

(72) Inventors: Eric Helms, Geneseo, NY (US); Jacqueline Bennett, Oneonta, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 17/234,715

(22) Filed: Apr. 19, 2021

(65) Prior Publication Data

US 2021/0323911 A1    Oct. 21, 2021

Related U.S. Application Data

(60) Provisional application No. 63/012,064, filed on Apr. 17, 2020.

(51) Int. Cl.
| | | |
|---|---|---|
| *C07C 249/08* | (2006.01) | |
| *C07C 249/16* | (2006.01) | |
| *C07D 241/44* | (2006.01) | |
| *C07D 241/42* | (2006.01) | |
| *C07C 249/02* | (2006.01) | |

(52) U.S. Cl.
CPC .......... *C07C 249/08* (2013.01); *C07C 249/02* (2013.01); *C07C 249/16* (2013.01); *C07D 241/42* (2013.01); *C07D 241/44* (2013.01); *C07C 2601/16* (2017.05)

(58) Field of Classification Search
CPC .................................................. C07C 249/08
See application file for complete search history.

(56) References Cited

U.S. PATENT DOCUMENTS

7,709,632 B2 *   5/2010   Johnson ............... C07D 291/08
                                                           540/145
8,766,004 B2 *   7/2014   Bennett ................. C07C 249/02
                                                           564/248

* cited by examiner

*Primary Examiner* — Golam M Shameem
(74) *Attorney, Agent, or Firm* — Peter Fallon; Lance Reich; Austin Winter

(57) ABSTRACT

The present disclosure relates to using green solvents to synthesize an array of imines, imine-related and imine-derived compounds in an efficient and eco-friendly matter, satisfying green chemistry requirements. Reaction embodiments are performed using solvents, such as ethyl lactate and dimethyl isosorbide, which are both individually characterized as green. In embodiments, solvents include lactic whey and/or water as co-solvents. In these green solvents, the synthesis process discussed herein can produce up to quantitative yields of product at room temperature in a short duration. Embodiments include a method of forming an imine, imine-related or imine-derived compound product. In embodiments, the methods include mixing an aldehyde reactant with a nucleophilic/nitrogen-containing reactant in a green solvent at a temperature between negative twenty degrees Celsius (−20° C.) and positive fifty degrees Celsius (50° C.); stirring the mixture; and forming an imine, imine-related or imine-derived compound product.

20 Claims, 28 Drawing Sheets

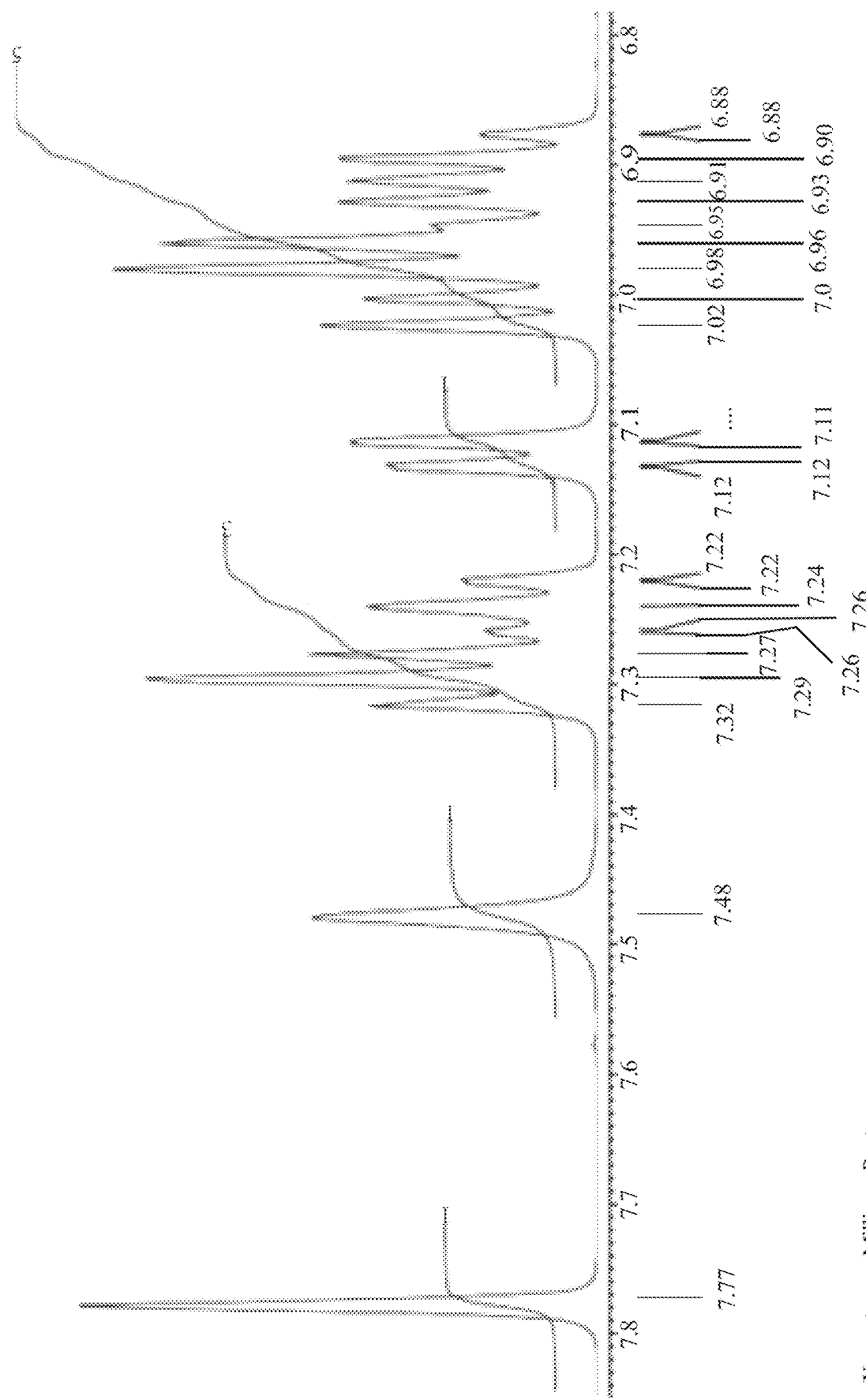

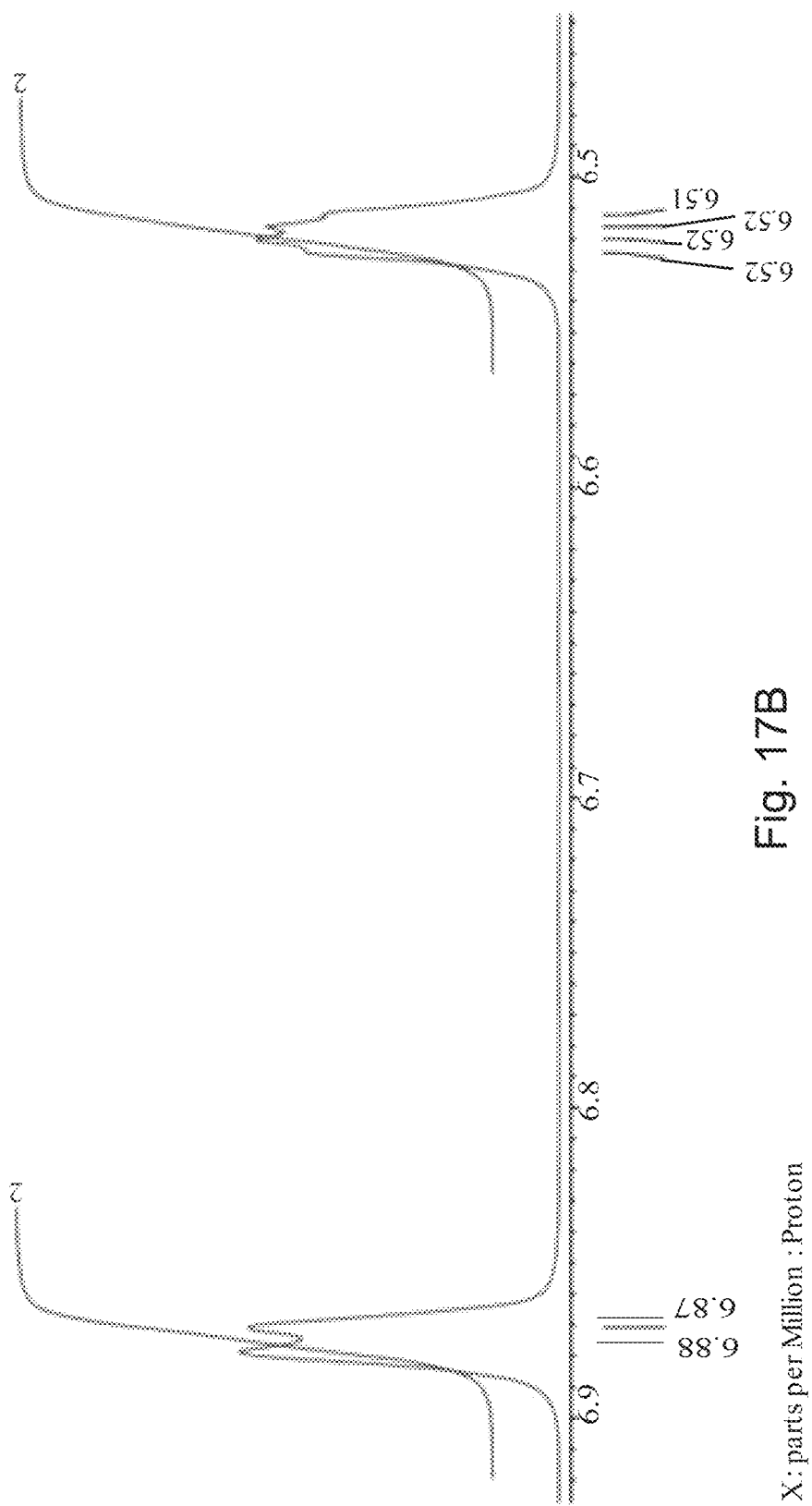

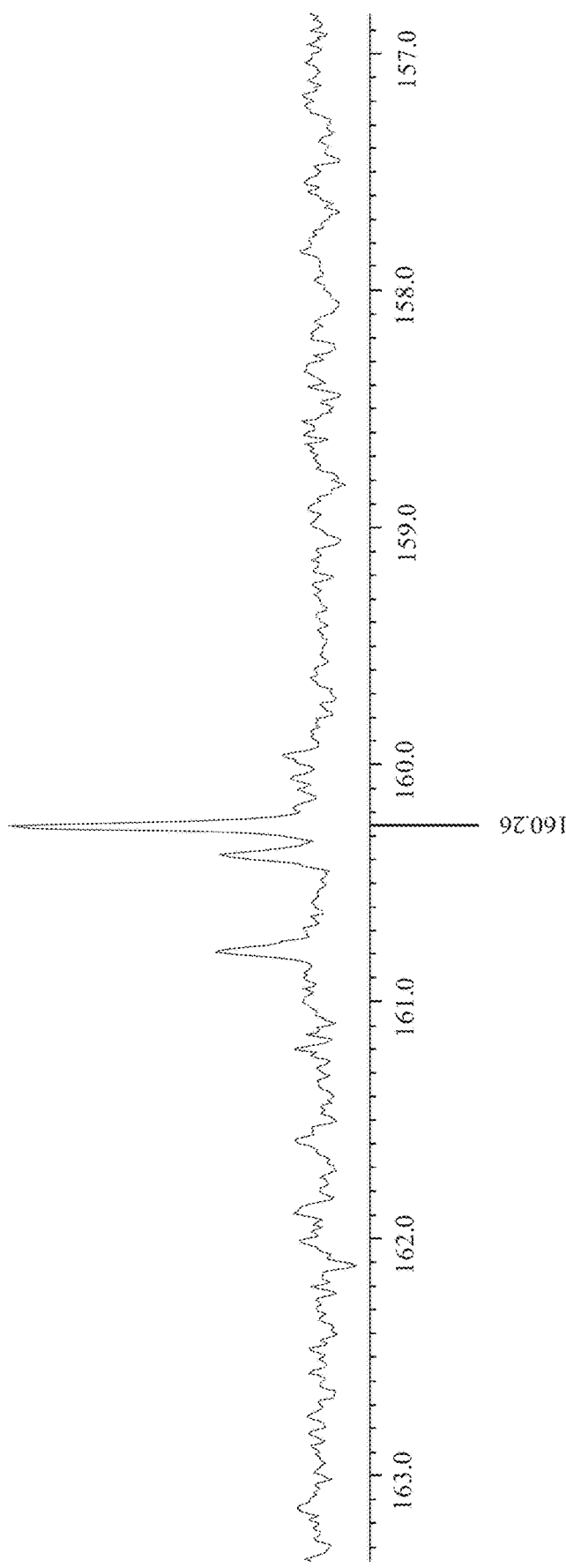

METHODS OF FORMING IMINES, IMINE-RELATED AND IMINE-DERIVED COMPOUNDS USING GREEN SOLVENTS

CROSS-REFERENCE TO RELATED APPLICATIONS

This application claims the benefit of the filing date of U.S. Provisional Application No. 63/012,064 filed Apr. 17, 2020. The content of this earlier filed application is hereby incorporated by reference herein in its entirety.

FIELD OF THE INVENTION

The present disclosure is in the field of organic chemistry and relates to methods for preparing imines, imine-related (e.g., azine, oxime, hydrazone, phenyl hydrazone, and semicarbazone) and/or imine-derived compounds that use environmentally friendly solvent systems. In embodiments, the field of the present disclosure relates to a solvent system using lactic whey as a co-solvent with ethyl lactate and methods of preparing one or more imines, or imine-related compounds such as azines, oximes, semicarbazones, 1,4-quinoxalines, and/or 1,4-quinoxalin-2-ones.

BACKGROUND

The imine, imine-related, and/or imine-derived compounds refer to classes of organic molecules that are of growing interest due to their versatile use in industry, agriculture, and pharmaceuticals such as for use in medicine and body metabolism. Imine-related and imine-derivatives have shown promise as components of several useful pharmaceutical molecules, some of which have antibiotic, anti-tumor/anti-cancer, anti-fungal, antibacterial, and anti-convulsant properties.

Conventional processes for forming imines, imine-related and imine-derived compounds typically include synthesis of imines, imine-related and imine-derived compounds over lengthy, high temperature reaction periods. Conventional synthesis processes also require the use of harmful reagents. Specifically, the reagents used in the conventional synthesis of imines, imine-related and imine-derived compounds are often toxic and nonenvironmentally friendly. For example, during the conventional processes, toxic reagents are often boiled for long periods of time and release toxic fumes into the environment. Additionally, the requirement to boil the mixture, including the toxic reagents, for long periods of time results in a large energy requirement.

Prior art of interest includes U.S. Pat. No. 8,766,004 entitled Green Synthesis of Aryl-Aldimines Using Ethyl Lactate to Bennett (herein entirely incorporated by reference) relating to forming an aryl aldimine. However, this system is deficient in that it does not contemplate certain imine-related and imine-derived compounds of the present disclosure, and there is no suggestion to use lactic whey in a solvent system. For example, this system did not envision the creation of quinoxalines or quinoxalinones or other imine-derived compounds either with or without lactic whey.

The disposal of whey, the liquid remaining after the separation of milk fat and casein from whole milk, continues to be a major problem for the dairy industry, which demands simple and economical solutions. Additional uses of the problematic byproduct lactic whey are needed to reduce waste and the accumulation of lactic whey.

There is a continuing need to remedy defects in chemical synthesis by providing compositions such as solvents and methods that are applicable to chemical synthesis, while being efficient, cost-sensitive, and environmentally friendly.

SUMMARY

In embodiments, the present disclosure provides compositions such as solvents, and methods for preparing imines, imine-related (e.g., azine, oxime, hydrazone, phenyl hydrazone, and semicarbazone) and/or imine-derived compounds such as quinoxalines or quinoxalinones that use environmentally friendly solvent systems.

In embodiments, the present disclosure includes a method of forming an imine, imine-related or imine-derived compound product, including the steps of: mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.), wherein the green solvent includes an aqueous solution of dimethyl isosorbide or an aqueous solution of ethyl lactate; stirring the mixture for a first duration; and forming an imine, imine-related or imine-derived compound product. In embodiments, the imine and/or imine-related compound is devoid of imines such as aryl aldimine. In embodiments, the imine-related compound is one or more of oxime, azine, hydrazone, phenylhydrazone, or semicarbazone.

In embodiments, the present disclosure includes a method of forming an imine-related compound product, including the steps of: mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.), wherein the green solvent includes an aqueous solution of dimethyl isosorbide or an aqueous solution of ethyl lactate; stirring the mixture for a first duration; and forming an imine-related compound product. In embodiments, the imine-related compound is devoid of imines such as aryl aldimine. In embodiments, the imine-related compound is one or more of oxime, azine, hydrazone, phenylhydrazone, or semicarbazone.

In embodiments, the present disclosure includes a method of forming an imine, imine-related, or imine derived compound product, including the steps of: mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.), wherein the green solvent includes lactic whey; stirring the mixture for a first duration; and forming an imine, imine-related, or imine derived compound product. In embodiments the lactic whey is one or more of acidic whey, sweet whey, or derivatives thereof.

In embodiments, the present disclosure includes a solvent suitable for use in the formation of an imine, imine-related or imine-derived compound product. In embodiments, the present disclosure includes a solvent suitable for use in the formation of an imine-related compound product. In embodiments, the solvent includes an aqueous solution including ethyl lactate and lactic whey. In embodiments the lactic whey is one or more of acidic whey, sweet whey, or derivatives thereof. In embodiments the lactic whey is one of acidic whey, sweet whey, or derivatives thereof. In embodiments the lactic whey is acidic whey.

In embodiments, the present disclosure includes a method of forming an imine, imine-related or imine-derived compound product, including: mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.) to form a mixture, wherein the green solvent comprises an aqueous solution of ethyl lactate and lactic whey; stirring the mixture for a first duration; and forming an imine, imine-related or imine-derived compound product. In embodiments, the lactic whey is acidic whey. In embodiments, the green solvent comprises an aqueous solution of ethyl lactate over a range of concentration ratios from 70:30 to 90:10, or 75:25 to 85:15 of ethyl lactate:lactic whey.

In embodiments, the present disclosure includes a solvent solution suitable for forming an imine, imine-related or imine-derived compound, or pharmaceutically acceptable salt thereof, including: an aqueous solution of ethyl lactate and lactic whey. In embodiments, the aqueous solution includes ethyl lactate over a range of concentration ratios from 70:30 to 90:10, or 75:25 to 85:15 of ethyl lactate:lactic whey. In embodiments, the lactic whey is acidic whey or sweet whey.

The illustrative aspects of the present disclosure are designed to solve the problems herein described and/or other problems not discussed.

BRIEF DESCRIPTION OF THE DRAWINGS

Non-limiting and non-exhaustive features will be described with reference to the following figures, wherein like reference numerals refer to like parts throughout the various figures. The figures below were not intended to be drawn to any precise scale with respect to size, angular relationship, or relative position.

FIGS. 13A and 13B depict the $^1$H NMR spectrum of salicylaldehyde phenylhydrazone ($CDCl_3$, 400 MHz).

FIGS. 17A and 17B depict the $^1$H NMR spectrum of 2-furaldehyde azine ($CDCl_3$, 400 MHz).

FIGS. 20A, 20B and 20C depict $^{13}$C NMR spectrum of salicylaldehyde azine ($CDCl_3$ with TFA for solubility, 400 MHz). Quartets are depicted, for the fluorine splitting in TFA but only the interior two peaks are visible for the $CF_3$ signal.

Figure 1:
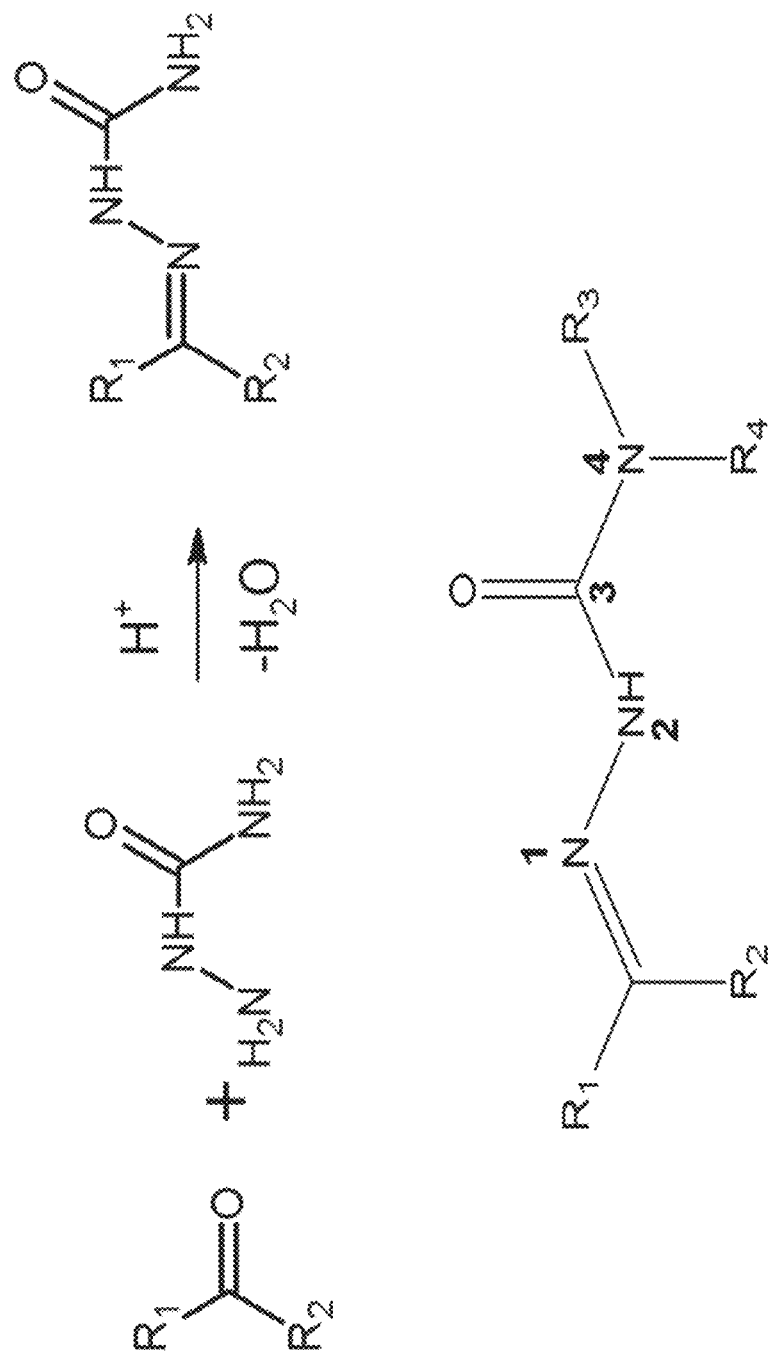
FIG. 1 depicts semicarbazone synthesis and a semicarbazone numbering scheme.
Figure 2:
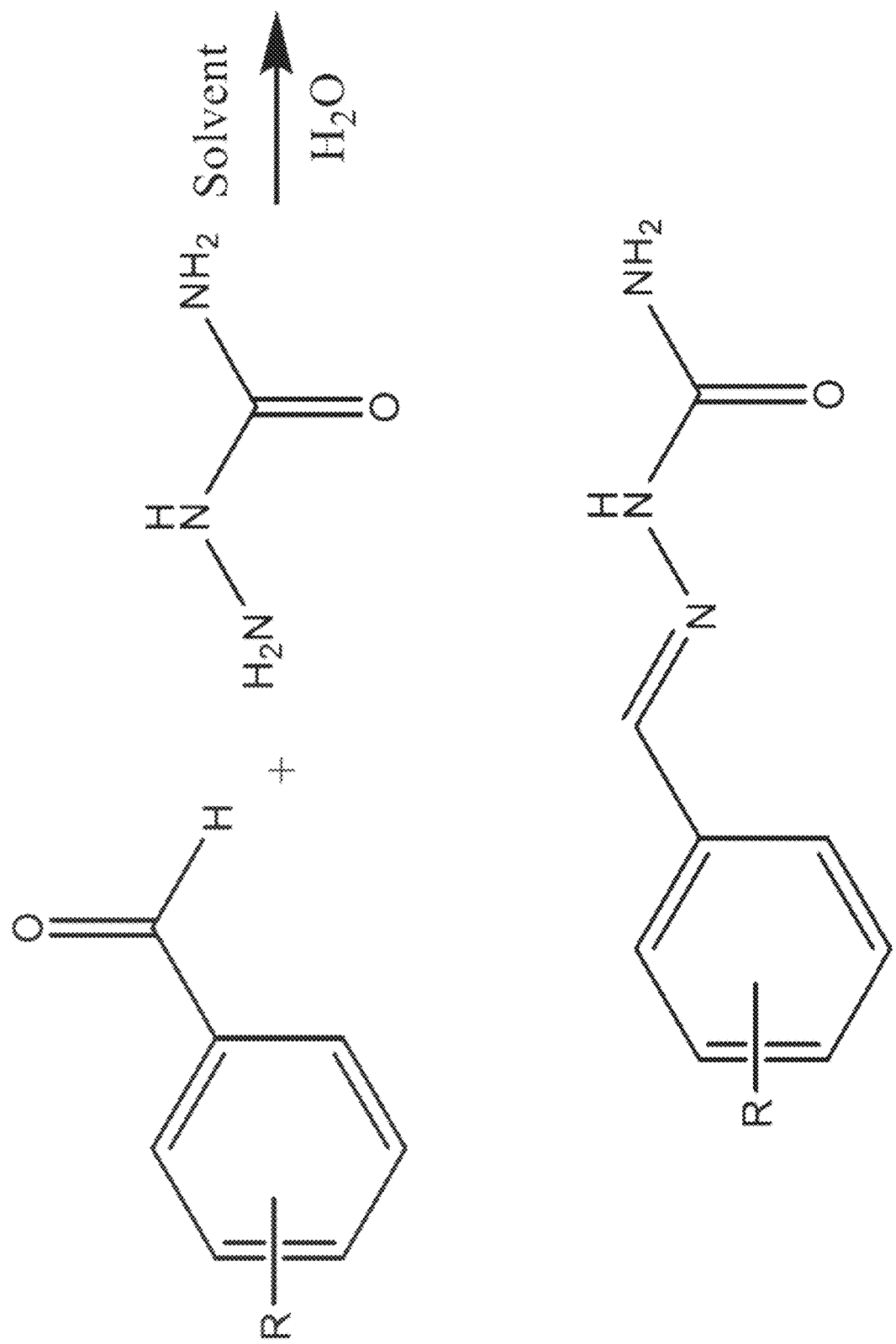
FIG. 2 depicts a reaction scheme for semicarbazone synthesis in accordance with the present disclosure where a substituted benzaldehyde and semicarbazide in the presence of water and either ethyl lactate or dimethyl isosorbide yields a semicarbazone.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION

In embodiments, the present disclosure provides compositions such as solvents, and methods for preparing imines, imine-related (e.g., azine, oxime, hydrazone, phenyl hydrazone, and semicarbazone) and/or imine-derived compounds that use environmentally friendly solvent systems. In embodiments, the present disclosure relates to solvent compositions and methods of forming an imine, imine-related or imine-derived compound or product, including the steps of: mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.), wherein the green solvent includes an aqueous solution of dimethyl isosorbide or an aqueous solution of ethyl lactate; stirring the mixture for a first duration; and forming an imine, imine-related or imine-derived compound product. In embodiments, stirring or mixing is performed under conditions sufficient to form one or more imine, imine-related or imine-derived compound products. In embodiments, conditions sufficient to form one or more imine, imine-related or imine-derived compound products may include solutions having a pH of 4-9. In embodiments, the first duration is 1 second to 1 hour. In embodiments, the green solvent includes ethyl lactate and lactic whey, and in some embodiments, a green solvent consists of a mixture of ethyl lactate and lactic whey. In embodiments, the green solvent includes ethyl lactate and acidic whey, and in some embodiments, a green solvent consists of a mixture of ethyl lactate and acidic whey.

Advantages of the present disclosure include compositions and methods that requires little to no energy input, including energy in the form of stirring and/or heat, requires no recrystallization of product, or other purification methods after formation of imine, imine-related or imine-derived compound product.

Definitions

As an initial matter, in order to clearly describe the current disclosure, it will become necessary to select certain terminology when referring to and describing relevant components within the disclosure. When doing this, if possible, common industry terminology will be used and employed in a manner consistent with its accepted meaning. Unless otherwise stated, such terminology should be given a broad interpretation consistent with the context of the present application and the scope of the appended claims. Those of ordinary skill in the art will appreciate that often a particular component may be referred to using several different or overlapping terms. What may be described herein as being a single part or constituent may include and be referenced in another context as consisting of multiple parts or constituents. Alternatively, what may be described herein as including multiple components or constituents may be referred to elsewhere as a single part.

The term "imine" refers to an organic compound containing the group —C═NH or —C═NR where R is an alkyl or other group.

The term "nucleophile" is recognized in the art, and as used herein means a chemical moiety having a reactive pair of electrons. Non-limiting examples of nucleophiles include uncharged compounds such as alcohols, imines, thiols, selenols, amines, and charged moieties such as alkoxides, thiolates, carbanions, and a variety of other organic anions.

The term "reaction product" means a compound which results from the reaction of reactants to form a stable product such as an imine, imine-related product, or imine-derived product. In general, the term "reaction product" will be used herein to refer to a stable, composition, and not to unstable intermediates or transition states.

The term "oxime" refers to any of various compounds containing the divalent group C═NOH and may be obtained e.g., by the action of hydroxylamine on aldehydes and ketones.

The term "azine" refers to a cyclic organic compound having a ring including one or more than one nitrogen atom.

The term "hydrazone" refers to any of a class of compounds containing the group >C═NNHR and may be formed by the action of hydrazine or a substituted hydrazine (as phenylhydrazine) on a compound containing a carbonyl group (as an aldehyde or ketone).

The term "phenylhydrazones" refers to a hydrazone derived from phenylhydrazine.

The term "semicarbazone" refers to a derivative of imines formed by a condensation reaction between a ketone or aldehyde and semicarbazide. In some embodiments, the semicarbazone may be classified as imine derivatives because they are formed from the reaction of an aldehyde or ketone with the terminal —$NH_2$ group of semicarbazide, which behaves very similarly to primary amines.

As used herein the term "quinoxaline" refers to a heterocyclic compound containing a ring complex made up of a benzene ring and a pyrazine ring. It is isomeric with other naphthyridines including quinazoline, phthalazine and cinnoline. In embodiments, quinoxaline is a naphthyridine in which the nitrogens are at positions 1 and 4.

As used herein the term "ethyl lactate" refers to a colorless water-soluble liquid ester $CH_3CH(OH)COOC_2H_5$ of low volatility.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In embodiments, a straight chain or branched chain alkyl has 30 or fewer carbon atoms in its backbone (e.g., $C_1$-$C_{30}$ for straight chain, $C_3$-$C_{30}$ for branched chain), and in embodiments, 20 or fewer. Likewise, in embodiments cycloalkyls have from 3-10 carbon atoms in their ring structure, and in embodiments have 5, 6 or 7 carbons in the ring structure. Moreover, the term "alkyl" (or "lower alkyl") is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, and in embodiments from one to six carbon atoms in its backbone structure. Likewise, "lower alkenyl" and "lower alkynyl" have similar chain lengths. In embodiments, alkyl groups are lower alkyls. In embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms "heterocyclyl" or "heterocyclic group" refer to 3- to 10-membered ring structures, and in embodiments 3- to 7-membered rings, whose ring structures include one to four heteroatoms. Heterocycles can also be polycycles.

Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. In embodiments, heteroatoms are nitrogen, oxygen, sulfur and phosphorous.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art recognized and refer to both unsubstituted and substituted amines, e.g., a moiety that can be represented by the general formula:

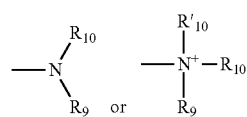

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In embodiments, only one of $R_9$ or $R_{10}$ can be a carbonyl, e.g., $R_9$, $R_{10}$ and the nitrogen together do not form an imide. In embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

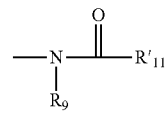

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

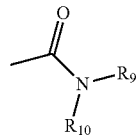

wherein $R_9$, $R_{10}$ are as defined above. In embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

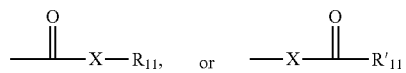

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R'_{11}$ is hydrogen, the formula represents a "thiolcarboxylic acid." Where X is a sulfur and $R_{11}$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

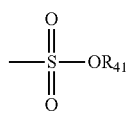

in which $R_{41}$ is an electron pair, hydrogen, alkyl, cycloalkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valencies of the heteroatoms. This disclosure is not intended to be limited in any manner by the permissible substituents of organic compounds.

The term "chiral" refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

For purposes of the present disclosure, the chemical elements are identified in accordance with the Periodic Table of the Elements, CAS version, Handbook of Chemistry and Physics, 67th Ed., 1986-87, inside cover. Also for purposes of this disclosure, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted. See also U.S. Pat. No. 6,072,085 herein entirely incorporated by reference.

The term "lactic whey" as used herein means a product that is produced by fermentation of milk, including skim milk, with lactic acid bacteria, for example, during the manufacture of casein, caseinate or cottage and ricotta cheeses. In embodiments lactic whey includes acidic whey or sweet whey. In embodiments, lactic whey refers to acidic whey.

The term "derivative of lactic whey" as used herein means a product derived from applying to lactic whey including lactic acid whey any of the commonly-used processes used in the dairy whey processing industry, such as a process to concentrate, fractionate or functionally enhance dairy whey. Concentration should be taken to mean any process that increases the level of solids in a feed whey stream from the native level or from that present in the feed whey stream at input, and may be accomplished by evaporation, membrane separation processes (including reverse osmosis, micro filtration and ultrafiltration), dehydration/drying processes and other processes known in the art. Fractionation processes intended are those that preferentially separate the inert or undesired elements of the whey stream from its functional or desired elements, including, for example, removal of superfluous lactose by crystallization, removal of unwanted fat by defatting (solvent extraction or other means known in the art), or preferential retrieval of functional protein isolates by affinity processes (affinity chromatography using appropriate media for whey proteins). Functional enhancement processes material to the current disclosure include demineralization, remineralization (e.g., changing the level of mineral species present in the product from their native levels and proportionate ratios, for example, by either dosing or by ion exchange), hydrolysis (of protein and/or lactose, by enzymic or chemical means generally known) or enzymic protein cross-linking. It is intended that in various representative embodiments a derivative of lactic whey or lactic acid whey is accomplished by performing any of these operations singly or by combining any two or more of these operations to produce a derivative of lactic whey such as acidic whey.

As used herein, the term "green" refers to components and/or methods that are environmentally friendly.

DETAILED DESCRIPTION OF CERTAIN EMBODIMENTS

In embodiments, a solvent(s) of the present disclosure includes renewable and/or biodegradable solvents. In embodiments, the solvent may be miscible with water and nonpolar organic solvents. In some embodiments, ethyl lactate, such as ethyl L-lactate, may be used as a solvent or constituent or portion of the solvent. In embodiments, ethyl lactate, water, and lactic whey (or a derivative or lactic whey) such as acidic whey is suitable for combined use as a solvent in accordance with the present disclosure. In embodiments, ethyl lactate, and acidic whey (or a derivative of acidic whey) is suitable for combined use as a solvent in accordance with the present disclosure.

In embodiments, a co-solvent may be added to the solvent of the system to alter the polarity of the system or allow the end product to crystallize out of the composition as it is formed, while the starting materials remain dissolved. In embodiments, water may be used as a polar co-solvent to increase solvent polarity and induce rapid formation of product. In embodiments, methanol or ethanol may be used as a polar co-solvent, though less polar than water, to increase solvent polarity and induce rapid formation of product.

In some embodiments, a co-solvent may include a nonpolar co-solvent to decrease solvent polarity and induce rapid formation of product. Through the present methods described in further detail below, imines, imine-related and imine-derived compounds have been found to be crystallized directly out of solution in high purity and yield, requiring no further purification. In embodiments, the solvents and solvent/co-solvent admixtures of the present disclosure are characterized as green such as being approved by the FDA as a food additive, being derived from renewable resources, and being biodegradable, making it a highly green material. The use of green solvents and green, environmentally efficient methods results in a more environmentally friendly process of forming the end products. In embodiments lactic whey and/or acidic whey is a co-solvent of the present disclosure for forming the imines, imine-related, and/or imine-derived compounds. In embodiments acidic whey includes a water constituent.

In embodiments, ethyl lactate is used as a solvent for forming the imines, imine-related, and/or imine-derived compounds of the present disclosure. Ethyl lactate is miscible with water as well as nonpolar organic solvents. Thus, a broad range of solvent polarity is accessible by simply "tuning" ethyl lactate with a cosolvent to create ideal conditions for rapid product formation. Thus, the compositions and methods of the present disclosure are capable of forming imines, imine-related, and/or imine-derived compounds through the use of a solvent over a broad polarity range. Polarity adjustment may be made by using a co-solvent, such as water, other polar solvent, or a nonpolar solvent. Such adjustment may be used for optimizing crystallizations. The present disclosure is capable of producing imines, imine-related, and/or imine-derived compounds under ambient conditions and processes so as to optimize reaction purity, yield, and speed. As used herein, the term "optimize" means to enhance effectiveness of one or more processes of the present disclosure, and not necessarily refers to formation of an end product that is 100% pure or gives 100% yield. The term "optimize" simply refers to producing an end product with a higher level of purity, yield, and/or speed than traditional processes.

In embodiments, the present disclosure includes a solvent combined with 0% to about 40% (by volume) water or other polar solvent. The combination of the solvent with water or other solvent is useful in controlling the polarity of the solvent. Any common solvent may be used, including solvents that are very polar, such as water, and those solvents that are nonpolar, such as limonene. Thus, in embodiments, the methods include adjusting the polarity of the solvent so as to efficiently prepare imines, imine-related, and/or imine-derived compounds. The present disclosure also provides a method of optimizing the polarity of the solvent through addition of co-solvents, such as water, to the green solvent used.

In embodiments, the present disclosure includes a solvent including ethyl lactate and lactic whey, a derivative thereof, or acidic whey or sweet whey.

In embodiments, the solvent including ethyl lactate and acidic whey, or a derivative thereof may further include water. Non-limiting examples of acidic whey include acid whey as described in U.S. Patent Publication No. US20180295847 entitled Manufacture Of Strained Fermented Dairy Products to De La Cruz et al published on 18 Oct. 2018 (herein entirely incorporated by reference). Accordingly, in embodiments, lactic whey includes acidic whey and describes a by-product formed during the fermentation of dairy products. In embodiments, acidic whey encompasses further processed compositions (e.g. filtered acid whey, neutralized acid whey and refined acid whey).

In some embodiments, lactic whey is considered a waste product from the production of cheese, yogurt, and other milk-derived products and is composed of water (~94% weight), the sugar lactose (~5% weight), proteins (~1% weight), minerals (~1% weight), and milk fat (~0.5% weight). In some embodiments, acidic whey may include or consist of from 0.0% to 0.4% by weight of protein, from 2.8% to 4.7% by weight of lactose, from 92.0% to 95% by weight of water, from 0.00% to 0.10% by weight of fat, and a pH of from 3.80 to 4.65. In some embodiments, acidic whey may include or consist of: 0.4% by weight of protein, such as whey protein, from 2.8% to 4.7% by weight of lactose, from 94.3% by weight of water, from 0.0% by weight of fat, and a pH of 4.5. In some embodiments, acidic whey may include or consist of from 0.0% to 5.0% by weight of protein, from 1.0% to 15% by weight of lactose, from 80.0% to 99% by weight of water, from 0.00% to 5.0% by weight of fat, and a pH of from 3.00 to 6.60. In embodiments, % weight refers to the percent weight of the total solvent composition.

In some embodiments, acidic whey includes about 4.2 to 4.9% (w/v) of lactose, about 93.5% (w/v) of water, about 0.55 to 0.75% (w/v) of protein, about 0.8% (w/v) of ash and about 0.04% (w/v) of lipids. In some embodiments, acidic whey of the present disclosure includes 4.2 to 4.9% (w/v) of lactose, 93.5% (w/v) of water, 0.55 to 0.75% (w/v) of protein, 0.8% (w/v) of ash and 0.04% (w/v) of lipids.

In embodiments, lactic whey such as acidic whey of the present disclosure is provided as a solvent, co-solvent, or diluent in the organic chemistry reactions of the present disclosure. In embodiments, lactic whey such as acidic whey is provided as a co-solvent for organic chemical reactions. In embodiments, the additional uses for lactic whey benefit at least, yogurt and cheese producers as well as producers of fine chemicals who want to use green chemistry.

In other embodiments, the present disclosure involves preparing one or more imines, imine-related, and/or imine-derived compounds through the use of less solvent volume than traditional methods for the same scale reaction. As used herein, the term "traditional methods" include methods that do not use green techniques, such as use of a green solvents or green methods described herein. For example, one "traditional method" includes formation of an imine, imine-related product or derivative through use of toluene as a solvent. In one aspect, the present disclosure provides a process of forming imines, imine-related, and/or imine-derived compounds by using about 10% of the solvent volume of traditional methods.

In another aspect, the present disclosure provides a process of preparing one or more imines, imine-related, and/or imine-derived compounds in shorter time than is required in traditional methods. For example, the present disclosure may be capable of forming imines, imine-related, and/or imine-derived compounds in about 30 seconds to about 10 minutes at about room temperature. In embodiments, the imine, imine-related or imine derived composition is formed in a duration of less than 10 minutes. In embodiments, the imine, imine-related or imine derived compound of the present disclosure is formed in a duration of 1 second to 1 hour. A traditional method, for example, may require more than 2 hours of reaction time to form the desired product.

Further, the present disclosure provides a process of preparing one or more imines, imine-related, and/or imine-derived compounds without having to purify the imines, imine-related, and/or imine-derived compounds after formation. Thus, desirably, after formation of the imines, imine-related, and/or imine-derived compounds, the imines, imine-related, and/or imine-derived compounds may be highly pure, such as at least 90% pure, at least 95% pure, or at least 99% pure. In embodiments, the resulting imines, imine-related, and/or imine-derived compounds is in excess of 98% pure. For example, the present disclosure may provide a process of forming one or more imines, imine-related, and/or imine-derived compounds without the need to evaporate or boil off the solvent used to prepare one or more imines, imine-related, and/or imine-derived compounds. The present disclosure may provide a process of forming one or more imines, imine-related, and/or imine-derived compounds without the need to recrystallize the one or more imines, imine-related, and/or imine-derived compounds after formation. In addition, the present disclosure may provide a process of forming one or more imines, imine-related, and/or imine-derived compounds without the need to use toxic solvents such as dichloromethane to purify the resulting product. For example, when ethyl lactate, lactic whey, acidic whey or combinations thereof are used as the solvent, the solvent may be filtered through the resultant crystals. Remaining residue may be washed off with water and the crystals allowed to air dry. In this instance, there is no need to heat the solvent to be evaporated from the one or more imines, imine-related, and/or imine-derived compounds, which saves energy costs, waste disposal costs, and other costs incurred, which may be extremely high especially on a large-scale process.

In embodiments, the present disclosure seeks to provide methods and processes for forming one or more imines, imine-related, and/or imine-derived compounds in environmentally friendly ways, such that the end product is useful and viable. In one aspect, the method results in one or more imines, imine-related, and/or imine-derived compounds that do not require further purification. Further, in another aspect, the method provides a method of forming one or more imines, imine-related, and/or imine-derived compounds that do not require additional heat during the processing steps. In yet another aspect, the present disclosure provides a method of forming one or more imines, imine-related, and/or imine-derived compounds without the requirement for a separate catalyst. Non-limiting examples of imines, imine-related, and/or imine-derived compounds are depicted in TABLE 1 below.

TABLE 1

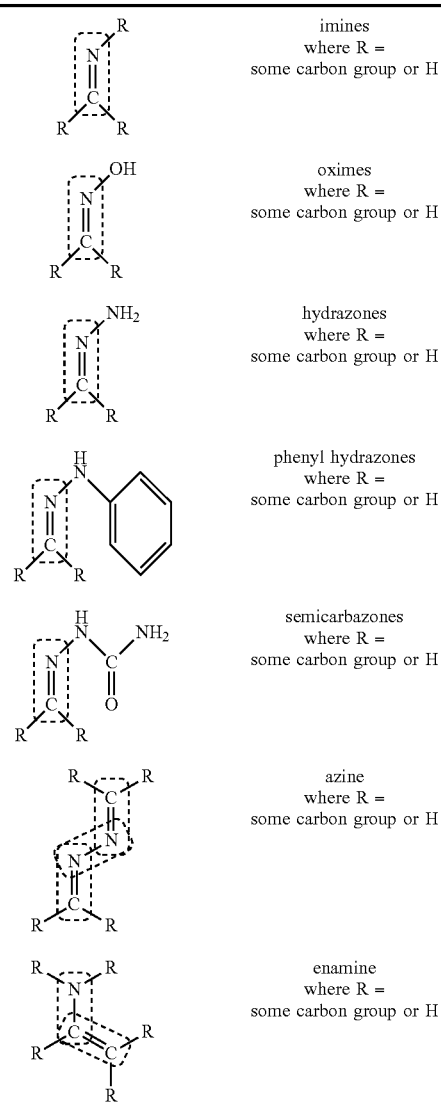

In embodiments, imines, oximes, hydrazones, phenyl hydrazones and semicarbazones are highly related as all share the core C=N bond and can be created by reacting a C=O compound with a N compound having just one bonded non-hydrogen group. See e.g., the equation below:

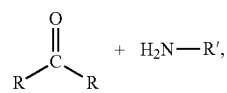

wherein R=a carbon group or H and R'=a group shown in Table 1 above.

In embodiments, azines are closely related to the hydrazones, including derivatives thereof, wherein the second $NH_2$ group has also reacted. Azines are closely related to the compound classes listed above. As shown above, azines may include, in embodiments, two C=N groups and a N—N single bond in the molecule.

In embodiments, enamines are assembled in a similar manner to the imines and related molecules, but with a change, wherein the N compound used includes two non-hydrogen groups bonded to the N atom (alternatively, only one H atom on the N atom. In the enamine pictured above a C=C and a C—N rather than a C=N is in the molecule.

In embodiments, enamines are formed as shown below:

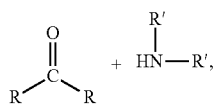

wherein R=a carbon group or H and R'=a carbon group.

In embodiments of the present disclosure, imine derived compounds include:

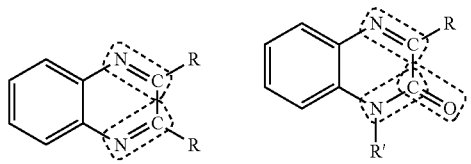

1,4-quinoxaline
where R = some carbon group or H 1,4-quinoxalin-2(1H)-one
where R = some carbon group or H and R' = H These two classes of compounds are assembled in a manner similar to imines, but only to a point. The N-containing component has two N atoms that each only have one carbon group on them and they must be on adjacent carbon atoms. The C=O component must have the C=O groups adjacent to one another, but differ in the functional groups present in the C=O containing component. These are related to the imines or other functional groups above.

In embodiments, 1,4-quinoxaline is formed by the reaction below:

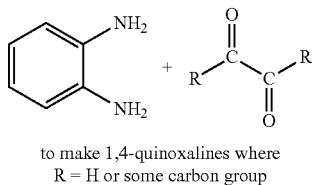

to make 1,4-quinoxalines where
R = H or some carbon group

In embodiments, 1,4-quinoxaline-2(1H)-ones is made by the reaction below:

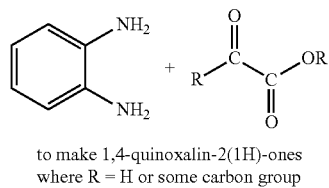

to make 1,4-quinoxalin-2(1H)-ones
where R = H or some carbon group

In embodiments, an aldehyde reactant selected from the group consisting of aromatic aldehyde, benzaldehyde, substituted benzaldehydes, aromatic ketone, acetophenone, and substitute acetophenone may be reacted with a primary amine, or a second reactant such as a second reactant is selected from the group consisting of semicarbazide hydrochloride, aqueous hydrazine, phenylhydrazine (not aqueous), and aqueous hydroxylamine.

The amount of starting amine will depend upon the amount of resulting imines, imine-related, and/or imine-derived compounds desired. For example, on a small-scale batch, anywhere from about 1 to about 100 mmol of the starting amine may be used. Larger amounts of starting materials will result in larger amounts of products such as imines, imine-related, and/or imine-derived compounds.

The starting amine may then be dissolved in the chosen solvent. As explained above, any solvent may be selected, and desirably the solvent is a green solvent. The solvent may be polarity-tuned by a cosolvent, if desired. In one particularly useful embodiment, the solvent may be ethyl lactate (such as ethyl L-lactate), and a polar cosolvent may be water. The resulting mixed solvent may have any desired polarity. The mixed solvent may include about 0 to about 40% of the polar solvent by weight of the mixed solvent, and more particularly may include about 5% polar solvent, 10% polar solvent, about 15% polar solvent, about 20% polar solvent, about 25% polar solvent, about 30% polar solvent, about 35% polar solvent or about 40% polar solvent by volume of the mixed solvent. For example, the mixed solvent may include 80% ethyl lactate and 20% water by volume of the mixed solvent. In embodiments, the amount of the mixed solvent is sufficient to drive the reaction forward. It may be desired to tune the polarity of the solvent mixture by adding more co-solvent until the desired level is reached.

In some embodiments, the mixed solvent may include 80% ethyl lactate and 20% lactic acid whey by volume of the mixed solvent. In embodiments, mixed solvent may include 95% ethyl lactate and 5% lactic acid whey by volume of the mixed solvent; 90% ethyl lactate and 10% lactic acid whey by volume of the mixed solvent; 70% ethyl lactate and 30% lactic acid whey by volume of the mixed solvent. In embodiments, ethyl lactate and lactic acid whey may be combined in a ratio of 99:1 or 1:99 by volume.

In some embodiments, the mixed solvent may include about 80% ethyl lactate and about 20% acid whey by volume of the mixed solvent. In embodiments, mixed solvent may include 95% ethyl lactate and 5% acid whey by volume of the mixed solvent; 90% ethyl lactate and 10% acid whey by volume of the mixed solvent; 70% ethyl lactate and 30% acid whey by volume of the mixed solvent. In embodiments, ethyl lactate and acid whey may be combined in a ratio of 99:1 or 1:99 by volume.

In embodiments, formation of a product in accordance with the present disclosure, includes, for example, after the starting amine is dissolved in the mixed solvent, an aldehyde (which may also be predissolved in the mixed solvent) may be added to the amine mixture. In embodiments, the aldehyde selected will depend upon the desired resulting imine. In embodiments, desirably the amount of aldehyde should be approximately equimolar to the amount of starting imine used to avoid purification to remove the component in excess following reaction. However, slight variations may be acceptable.

In embodiments, for example, if the desired resulting imine is cinnamylidine aniline, the starting amine is desirably aniline and the starting aldehyde is desirably cinnamaldehyde.

This reaction mixture may be stirred, mixed or swirled until approximately homogenous and then allowed to sit undisturbed for the desired length of time. The reaction time may be from about 10 seconds to about 10 minutes, if desired. In embodiment, the initial swirling time be lower than the time to be sit undisturbed, and most desirably is about 2-5 seconds. The length of time that the mixture is allowed to sit undisturbed may be any time from about 30 seconds to about 20 minutes, and more particularly about 1 to about 10 minutes or from about 1 to about 5 minutes. Most desirably, the time to sit undisturbed is less than 10 minutes. The swirling and sitting stages are desirably performed at about room temperature. During the time that the reaction mixture is allowed to sit undisturbed, imine crystals will form. In some embodiments, it may be useful to slightly chill the mixture after it has been allowed to sit at room temperature for the desired length of time. For example, the mixture may be chilled in an ice bath at about 0° C. for less than five minutes.

In embodiments, when crystallization is complete (i.e., at the end of the time period allowed to sit undisturbed), the crystals may be harvested. Any desired harvesting may be used, so as to gather the resulting crystals. In one embodiment, crystals may be chilled on ice. Another aspect of harvesting includes rinsing the crystals with a rinsing agent, such as brine and/or water. The crystals may be vacuum filtered if desired. Crystals may be allowed to air dry. For example, crystals may be chilled, rinsed with brine and vacuum filtered, then washed with cold water and allowed to air dry. It may be necessary to desiccate the resulting crystals to fully remove water, particularly when humidity levels are high and the imine contains a hygroscopic moiety, such as a hydroxy group.

The resulting crystalline imine is desirably highly pure and thus avoids the need for recrystallization. Therefore, there is no need to take steps to further purify the resulting imine. After the resulting imines, imine-related, and/or imine-derived compounds is formed, it may be used as a starting material for one of any number of final compounds, including, for example, antibiotics, cholesterol-lowering drugs, or acrylate monomers used to make various acrylate-based polymers. Thus, in some embodiments, the present disclosure provides methods of forming such final compounds using energy efficient, green methods described above.

The present disclosure further provides imines, imine-related, and/or imine-derived compounds imine formed by the processes described above. The imines, imine-related, and/or imine-derived compounds is desirably formed with attention to green principles, such as using green starting materials, green catalysts, energy efficient methods, waste reduction methods, and the like.

In embodiments, the present disclosure includes combining one or more carbonyl-containing compounds with one or more nitrogen-containing compounds to produce imines, imine-related and imine-derived compounds. In the synthesis of imines, oximes, azines, hydrazones, phenylhydrazones, semicarbazones, the carbonyl-containing component includes but is not limited to an aromatic aldehyde or vinylogous aromatic aldehyde or aromatic ketone or vinylogous aromatic ketone; or an arene such as an aromatic hydrocarbon that may contain additional functional groups such as alcohols, halides, carboxylic acids, tertiary amines, ethers, esters, alkyl groups, alkenyl groups, alkynyl groups; or the arene may be a substituted heterocycle such as 2-pyridyl or 4-pyridyl.

In embodiments, the one or more nitrogen-containing compounds or components include an aromatic primary amine, or hydroxylamine, a butyl amine (primary aliphatic amine) or hydroxylamine aqueous solution, or hydroxylamine hydrochloride, or hydroxylamine hydrochloride aqueous solution, or hydrazine, or aqueous hydrazine solution, or a monosubstituted hydrazine, or phenylhydrazine, or semicarbazide hydrochloride, or semicarbazide hydrochloride aqueous solution, or ethylene diamine. In embodiments, one or more nitrogen-containing compounds or components include butyl amine such as primary aliphatic amine, or enamine such as aliphatic secondary amine).

In embodiments, for example in the synthesis of enamine compounds, the one or more carbonyl-containing components include a ketone or aldehyde with at least one hydrogen atom attached to the alpha-carbon relative to the carbonyl group or a 1,3-dicarbonyl compound such as 2,4-pentanedione. In embodiments, the one or more nitrogen-containing compounds or components include a secondary amine or an aromatic amine or a substituted aromatic amine.

In embodiments, for example in the synthesis of 1,4-quinoxalines or quinoxalin-2(1H)-ones, the carbonyl-containing component includes a 1,2-dicarbonyl compound, where the carbonyl moieties are part of an aldehyde, ketone, ester, or carboxylic acid functional group or a combination of these functional groups and the nitrogen-containing component includes an aromatic 1,2-diamine or a singly- or multiply-substituted aromatic 1,2-diamine.

In embodiments, the present disclosure relates to the green synthesis of enamine compounds. During the formation of enamines, a transient iminium ion forms, which undergoes beta-elimination to produce the enamine rather than the imine due to the structure of the nitrogen-containing component in the case of the use of secondary amines or due to the greater stability conferred on the product by intramolecular hydrogen bonding in the case of an aromatic amine reacting with a 1,3-dicarbonyl compound.

In embodiments, the present disclosure relates to the synthesis/formation of imines, imine-related and imine-derived compounds. Imines, imine-related and imine-derived compounds, sometimes referred to as Schiff-base compounds or azomethine, may refer to any C=N compound, including, but not limited to the example compounds discussed herein.

In non-limiting examples, the methods described herein may be useful in the formation of imine-related compounds products, including but not limited to oximes, enamines, hydrazones (e.g., phenylhydrazones), azines, quinoxalines, quinoxalinones, and/or semicarbazones. For example, in embodiments, the methods described herein may be useful in the formation of imine-related compounds products comprising or consisting of oximes; the methods described herein may be useful in the formation of imine-related compounds products comprising or consisting of enamines; the methods described herein may be useful in the formation of imine-related compounds products including or consisting of hydrazones; the methods described herein may be useful in the formation of imine-related compounds products including or consisting of azines; the methods described herein may be useful in the formation of imine-related compounds products including or consisting of quinoxalines; or methods described herein may be useful in the formation of imine-related compounds products including or consisting of semicarbazones. Examples of semicarbazones include 4-hydroxybenzaldehyde semicarbazone, 1-naphthaldehyde semicarbazones, 4-chlorobenzaldehyde semicarbazone, cuminaldehyde semicarbazone, 4-nitrosalicylaldehyde semicarbazone, and vanillin semicarbazone.

In embodiments, imine-related compounds include oximes, enamines, hydrazones (e.g., phenylhydrazones), azines, quinoxalines, quinoxalinones, and semicarbazones including, but not limited to, 4-hydroxybenzaldehyde semicarbazone, 1-naphthaldehyde semicarbazones, 4-chlorobenzaldehyde semicarbazone, cuminaldehyde semicarbazone, 4-nitrosalicylaldehyde semicarbazone, and vanillin semicarbazone. In embodiments, imine-related compounds include or consist of oximes. In embodiments, imine-related compounds consist enamines. In embodiments, imine-related compounds consist of hydrazones (e.g., phenylhydrazones). h embodiments, imine-related compounds consist of azines. In embodiments, imine-related compounds consist d one or more quinoxalines. In embodiments, imine-related compounds consist done or more quinoxalinones. In embodiments, mine-related compounds consist d and semicarbazones including, but not limited to, 4-hydroxybenzaldehyde semicarbazone, 1-naphthaldehyde semicarbazone, 4-chlorobenzaldehyde semicarbazone, cuminaldehyde semicarbazone, 4-nitrosalicylaldehyde semicarbazone, and vanillin semicarbazone.

In embodiments, a method of forming an imine-related compound product, includes the steps of: mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.), wherein the green solvent includes an aqueous solution of dimethyl isosorbide or an aqueous solution of ethyl lactate, wherein the first reactant is an aldehyde reactant selected from the group consisting of aromatic aldehyde, benzaldehyde, substituted benzaldehydes, aromatic ketone, acetophenone, and substitute acetophenone, and wherein the second reactant is selected from the group consisting of semicarbazide hydrochloride, aqueous hydrazine, phenylhydrazine (not aqueous), and aqueous hydroxylamine; stirring the mixture for a first duration; and forming an imine-related compound product, wherein the imine-related compound is one of semicarbazone, azine, phenylhydrazone, or oxime.

In embodiments, a method of forming a semicarbazone, includes the steps of: mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.), wherein the green solvent comprises an aqueous solution of dimethyl isosorbide or an aqueous solution of ethyl lactate, wherein the first reactant is an aldehyde reactant comprising aromatic aldehyde, benzaldehyde, substituted benzaldehydes, aromatic ketone, acetophenone, and substitute acetophenone, and wherein the second reactant is semicarbazide hydrochloride, stirring the mixture for a first duration; and forming a semicarbazone.

In embodiments, a method of forming an azine compound product, includes the steps of: mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.), wherein the green solvent comprises an aqueous solution of dimethyl isosorbide or an aqueous solution of ethyl lactate, wherein the first reactant is an aldehyde reactant selected from the group consisting of aromatic aldehyde, benzaldehyde, substituted benzaldehydes, aromatic ketone, acetophenone, and substitute acetophenone, and wherein the second reactant is aqueous hydrazine; stirring the mixture for a first duration; and forming an azine compound product.

In embodiments, a method of forming a phenylhydrazone compound product, includes the steps of: mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.), wherein the green solvent comprises an aqueous solution of dimethyl isosorbide or an aqueous solution of ethyl lactate, wherein the first reactant is an aldehyde reactant selected from the group consisting of aromatic aldehyde, benzaldehyde, substituted benzaldehydes, aromatic ketone, acetophenone, and substitute acetophenone, and wherein the second reactant is phenylhydrazine (not aqueous); stirring the mixture for a first duration; and forming a phenylhydrazone compound product.

In embodiments, the present disclosure includes a method of forming an oxime, including the steps of: mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.), wherein the green solvent comprises an aqueous solution of dimethyl isosorbide or an aqueous solution of ethyl lactate, wherein the first reactant is an aldehyde reactant selected from the group consisting of aromatic aldehyde, benzaldehyde, substituted benzaldehydes, aromatic ketone, acetophenone, and substitute acetophenone, and wherein the second reactant is aqueous hydroxylamine; stirring the mixture for a first duration; and forming an oxime compound product.

It will be understood by one of skill in the art that the present methods are not limited to the examples discussed herein, however, and may be useful in preparing a variety of imines, imine-related and imine-derived compounds. Additionally, the methods and products described herein are made in consideration of environmentally friendly ("green") principles.

In some embodiments, the present methods may include the use of green solvents. The green solvents may include, but are not limited to, ethyl lactate and/or dimethyl isosorbide (DMI). In still other embodiments, the present methods may include the use of green processing methods, such as energy efficient methods (e.g., no boil requirement) and methods that reduce waste. Optimally, the methods described herein include combinations of green solvents, and green processing methods.

The present disclosure also relates to a greener synthesis of imines, imine-related and imine-derived compounds, such as by using green solvents. Environmentally friendly "green" chemistry seeks to include methods that reduce or eliminate waste products, reduce or eliminate the use of toxic or hazardous solvents and procedures, avoid using energy-consuming methods, use renewable resources, increase energy efficiency, use components that are biodegradable and preferably minimize accident potential. Desirably, the components in the methods of the present disclosure, including the solvent, co-solvent and any other materials used to form the end product may have "green" features or attributes. Features of "green" compounds include, among others, the following: they may be approved by the FDA (or applicable governmental regulatory agency) (e.g., ethyl lactate) as a food additive; may be derived from renewable resources; and may be biodegradable. Such characteristics of the components may help define just how environmentally friendly (or "green") the component is. A highly green material possesses each of the foregoing features, a moderately green material may include two of the features described above, and a slightly green material may include one of the features described above.

In embodiments, at least a moderately green material is used and embodiments include a highly green material in the present disclosure. As discussed herein, the green solvents used in the synthesis of imines, imine-related and imine-derived compounds may include ethyl lactate and/or dimethyl isosorbide (DMI). In some embodiments, the solvents comprise lactic whey, ethyl lactate, and/or water.

However, it is understood that additional green material may be used in the process of synthesizing imines, imine-related and imine-derived compounds. That is, the methods and processes of the disclosure are not limited to use of the green solvents explicitly discussed herein. Rather, one skilled in the art would understand that other green material or solvents, such as ethyl acetate, may be used in the process of synthesizing imines, imine-related and imine-derived compounds. In embodiments, the green solvents discussed herein are merely examples of green solvents that may utilized in the synthesis of imines, imine-related and imine-derived compounds.

In embodiments, the green methods discussed herein may provide synthesis of imines, imine-related and imine-derived compounds that require little to no energy input, including energy in the form of stirring and/or heat, requires no recrystallization of product, and/or other purification methods after formation of the product. Although achievement of each goal is desired, it may be understood that achievement of one or more of the stated goals is acceptable.

In non-limiting examples for synthesizing imines, imine-related and imine-derived compounds, the process may include mixing an aldehyde reactant, a nucleophilic reactant or nitrogen-containing reactant, and a green solution. The aldehyde reactant may be formed and/or include any suitable aldehyde reactant material that may aid in the synthesis of imines, imine-related and imine-derived compounds as discussed herein.

For example, aldehyde reactant may include, but is not limited to, aromatic aldehydes such as benzaldehyde, and substituted benzaldehydes or aromatic ketones, such as acetophenones and substitute acetophenones. nucleophilic reactant or nitrogen-containing reactant may include any suitable reactant based on a desired or preselected imine, imine-related and imine-derived compound that is being synthesized. For example, semicarbazide hydrochloride may be used to synthesize semicarbazones, aqueous hydrazine to synthesize azines, phenylhydrazine (not aqueous) to synthesize phenylhydrazones, and aqueous hydroxylamine to synthesize oximes. In some non-limiting examples, nucleophilic reactant or nitrogen-containing reactant may also require the addition of, for example, lactic acid as a catalyst for the synthesis process. Additionally, the green solution may include, but is not limited to, ethyl lactate and/or dimethyl isosorbide (DMI).

As discussed herein, synthesizing imines, imine-related and imine-derived compounds may include mixing an aldehyde reactant with a nucleophilic reactant or nitrogen-containing reactant in a green solution. In a non-limiting example, each of the three materials or compositions used in synthesizing imines, imine-related and imine-derived compounds may be prepared separately and mixed in sequence and/or succession.

For example, a green solvent or green solvent mixture may first be prepared. That is, a predetermined amount of green solvent may be measured in provided in a first container (e.g., beaker), or alternatively a green solvent mixture, including a predetermined amount of green solvent and water, may be provided in the container.

As discussed herein, the ratio of green solvent and water may vary and/or may be dependent, at least in part, on the composition of the green solvent used and/or the composition of the composition of the reactant(s) used to synthesize imines, imine-related and imine-derived compounds.

Once the green solvent or the green solvent mixture is prepared, a predetermined portion of the green solvent or green solvent mixture may be added to a predetermined amount of the aldehyde reactant in a second container, distinct from the first container. The mixture in the second container may be referred to as a (aqueous) green solvent aldehyde solution.

Subsequently or simultaneously, a predetermined portion of the green solvent or green solvent mixture may be added to a predetermined amount of the nucleophilic reactant or nitrogen-containing reactant in a third container; distinct from the first and second containers. In other non-limiting examples, a predetermined amount of water may be added to a predetermined amount of the nucleophilic reactant or nitrogen-containing reactant in the third container. In either non-limiting example, the mixture in the third container may be referred to as an (aqueous) nucleophilic/nitrogen-containing solution.

As discussed herein the first container may include only the green solvent, or alternatively may include a mixture of green solvent and water. The ratio of green solvent to water may vary and/or may be dependent, at least in part, on the composition of the green solvent used and/or the composition of the composition of the reactant(s) used to synthesize Imines, Imine-related and Imine-derived compounds. In general, the ratio of green solvent to water may range from approximately 60:40 of green solvent to water to 100:0. Where the green solvent includes an aqueous solution of ethyl lactate, the ratios may include approximately 60:40 of ethyl lactate to water to 100:0.

In other non-limiting examples, the ratios may include approximately 70:30 of ethyl lactate to water to approximately 90:10, approximately 75:25 of ethyl lactate to water to approximately 85:15, or specifically approximately 80:20 of ethyl lactate to water.

In other non-limiting examples, the ratios may include approximately 70:30 of ethyl lactate to lactic whey such as acidic whey to approximately 90:10, approximately 75:25 of ethyl lactate to lactic whey to approximately 85:15, or specifically approximately 80:20 of ethyl lactate to lactic acid whey.

Where the green solvent includes an aqueous solution of dimethyl isosorbide, the ratios may include approximately 85:15 of dimethyl isosorbide to water to 100:0. In other non-limiting examples, the ratios may include approximately 90:10 of dimethyl isosorbide to water to approximately 95:5, or specifically approximately 92:8 of dimethyl isosorbide to water.

In a non-limiting example where the material is (initially) prepared separate from one another, the contents of each container may then be combined. More specifically, the content of the second container including the predetermined portion of the green solvent or green solvent mixture and the predetermined amount of the aldehyde reactant may be combined and/or added to the third container including predetermined portion of the green solvent or green solvent mixture (or water) and the predetermined amount of the nucleophilic reactant or nitrogen-containing reactant.

The combined content of the second container and the third container may be referred to herein as the reaction solution. In a non-limiting example, and if applicable, any remaining green solvent or green solvent mixture included in the first container may be added to the (now empty) second container.

The remaining green solvent or green solvent mixture may be used to "rinse" or mix with any remaining mixture included in the second container, and then provided to the third container including the reaction solution. In other non-limiting examples, the reaction solution may be further processed as discussed herein to provide the synthesis of Imines, Imine-related and Imine-derived compounds without the addition of the remaining green solvent or green solvent mixture.

Once combined, the reaction solution may undergo various processes to allow chemical reaction between the materials included therein. In one non-limiting example the reaction solution included in the third container may be mixed and/or stirred to combine the material forming reaction solution.

Additionally, or in another non-limiting example, reaction solution included in the third container may be mixed and/or stirred until a homogenous mixture of the materials is formed. Alternatively, the reaction solution may not be mixed or stirred and may have additional processed performed subsequently to combining the materials or compositions to initiate a chemical reaction between the materials.

After combining, mixing, and/or stirring the reaction solution, the reaction solution may rest. That is, after forming (and subsequently mixing) the reaction solution, the third container including the reaction solution may rest, be idle, and/or be undisturbed for a predetermined period of time. In a non-limiting example, the reaction solution may rest for a predetermined period of time at room temperature. The predetermined period of time may be dependent, at least in part, on the composition of the reaction solution.

Reaction solution may also undergo a chilling or cooling process. That is, the reaction solution included within the third container may undergo a chilling or cooling process after being combined, mixed, and/or stirred. Chilling or cooling the reaction solution may result in crystallization of the solution.

In non-limiting examples, the reaction solution may be chilled using a freezer, a cold plate, or other suitably systems/devices for cooling the solution. In another non-limiting example, the reaction solution may be chilled or cooled by submerging the third container in an ice bath.

The reaction solution may be cooled or chilled for a predetermined period of time, which may be dependent, at least in part, on the composition of the reaction solution. In a non-limiting example, the reaction solution may be cooled to between approximately twenty degrees Celsius (20° C.) and approximately negative twenty degrees Celsius (−20° C.).

In one non-limiting example, once chilled and cooled, and the reaction solution undergoes a crystallization process, the crystallized reaction solution or crystals formed therein may form the synthesized Imines, Imine-related and Imine-derived compounds. In this non-limiting example, the synthesized Imines, Imine-related and Imine-derived compounds may be extracted and utilized as discussed herein.

In another non-limiting example, the crystallized reaction solution may undergo additional processes to synthesize Imines, Imine-related and Imine-derived compounds. For example, once crystallized and/or chilled, the reaction solution may be filtered. The crystallized reaction solution may be filtered to separate any generated or formed solids from the remaining liquid of in the reaction solution. In non-limiting examples, the reaction solution may be filtered using a Hirsch or Buchner funnel. However, it is understood that the solid product may be filtered and collected from the remaining liquid in the crystallized reaction solution using any suitable filtering device and/or system.

Once filtered, the solid product filtered from the crystallized reaction solution may be dried. Specifically, the collected, solid product may be dried for a predetermined period of time. In a non-limiting example, the collected or filtered solid product may be dried in a vacuum oven for the predetermined period of time.

Once dried, the remaining solid product may include the synthesized Imines, Imine-related and Imine-derived compounds. That is, drying the solid product filtered from the crystallized reaction solution may form the desired, synthesized Imines, Imine-related and Imine-derived compounds. To improve the purity and/or synthesized Imines, Imine-related and Imine-derived compounds, the filtered solid product from the crystallized reaction solution may be washed with a solution (e.g., distilled water, ice water) prior to drying the product.

Additional processes may be performed on the various materials and/or compositions that are used to synthesize Imines, Imine-related and Imine-derived compounds, as discussed herein. That is, in addition to the processes discussed herein, additional and/or intermediate processes may be performed on one or more the materials and/or compositions used to synthesize Imines, Imine-related and Imine-derived compounds. For example, before mixing the green solvent or the green solvent solution with the aldehyde reactant in the second container, the green solvent or the green solvent solution may be heated. More specifically, the green solvent or the green solvent solution may be heated above room temperature to as high as fifty degrees Celsius (50° C.), prior to being added to the aldehyde reactant.

As a result of heating the green solvent or the green solvent solution, when added to the aldehyde reactant, a supersaturated green solvent aldehyde solution may be formed in the second container. In this non-limiting example, the aqueous nucleophilic/nitrogen-containing solution is mixed into the supersaturated green solvent aldehyde solution within zero (0) to approximately thirty (30) seconds after the aldehyde reactant is totally dissolved and completely enters solution in the green solvent or green solvent mixture.

In other non-limiting examples, the green solvent or the green solvent solution may be mixed with the aldehyde reactant in the second container to form the green solvent aldehyde solution, which then may be heated. Once heated, the aqueous nucleophilic/nitrogen-containing solution may be mixed with the green solvent aldehyde solution, as similarly discussed herein.

In another non-limiting example, the nucleophilic/nitrogen-containing solution and/or the green solvent aldehyde solution may be cooled prior to mixing or combining to form the reaction solution. That is, one or both of the nucleophilic/nitrogen-containing solution and the green solvent aldehyde solution may be cooled prior to mixing the two solutions together to form the reaction solution. In the non-limiting example, the nucleophilic/nitrogen-containing solution and/or the green solvent aldehyde solution may be cooled to between approximately twenty degrees Celsius (20° C.) and approximately negative twenty degrees Celsius (−20° C.) prior to mixing or combining.

In additional non-limiting examples, a predetermined amount of water may be mixed with the nucleophilic/nitrogen-containing solution, the green solvent aldehyde solution, and/or the reaction solution. In one instance, and prior to mixing the nucleophilic/nitrogen-containing solution and the green solvent aldehyde solution to form the reaction solution, water may be added to and mixed with the nucleophilic/nitrogen-containing solution and/or the green solvent aldehyde solution. Additionally, or alternatively, water may be added to the reaction solution formed by combining the nucleophilic/nitrogen-containing solution and the green solvent aldehyde solution.

In other non-limiting examples, a brine may be mixed with the nucleophilic/nitrogen-containing solution, the green solvent aldehyde solution, and/or the reaction solution. In one instance a saturated brine may be mixed with one or both of the nucleophilic/nitrogen-containing solution and the green solvent aldehyde solution prior to combining to form the reaction solution.

Additionally, or alternatively, a saturated brine may be added to the reaction solution formed by combining the nucleophilic/nitrogen-containing solution and the green solvent aldehyde solution. In another non-limiting example, the (saturated) brine may be chilled prior to adding and mixing the chilled brine with the nucleophilic/nitrogen-containing solution, the green solvent aldehyde solution, and/or the reaction solution.

As a result of mixing the identified materials or composition with the chilled brine, the nucleophilic/nitrogen-containing solution, the green solvent aldehyde solution, and/or the reaction solution may also undergo a chilling or cooling process while being mixed with the chilled brine. In a further non-limiting example, a saturated brine may be mixed with the nucleophilic/nitrogen-containing solution, and the mixture of saturated brine and nucleophilic/nitrogen-containing solution may be subsequently cooled.

The combined mixture of the saturated brine and the nucleophilic/nitrogen-containing solution may cooled to between approximately twenty degrees Celsius (20° C.) and approximately negative twenty degrees Celsius (−20° C.) prior to mixing the green solvent aldehyde solution with the saturated brine and aqueous nucleophilic/nitrogen-containing solution mixture.

In the non-limiting examples discussed herein, the brine may be a saturated brine or alternatively a supersaturated brine that may be brought to a temperature within a range of between approximately negative twenty degrees Celsius (−20° C.) and approximately positive twenty degrees Celsius (20° C.).

Although discussed herein a specific order, synthesized imines, imine-related and imine-derived compounds may be performed in distinct order. That is, other non-limiting examples may form the reaction solution in a distinct order than forming the nucleophilic/nitrogen-containing solution and the green solvent aldehyde solution separately, as discussed herein.

For example, the nucleophilic reactant or nitrogen-containing reactant and the aldehyde reactant may be first combined and then subsequently provided to the green solvent mixture to form the reaction solution. Alternatively, the nucleophilic reactant or nitrogen-containing reactant and the aldehyde reactant may each be disposed, mixed, and/or provided to the green solution mixture, directly and separately, to form the reaction solution.

In another non-limiting example, only one of the nucleophilic/nitrogen-containing solution or the green solvent aldehyde solution may be formed, prior to adding the remaining reactant to the solution. That is, in one example, the nucleophilic/nitrogen-containing solution may be formed as similarly discussed herein.

Once formed the aldehyde reactant may be combined and/or mixed directly with the nucleophilic/nitrogen-containing solution, along with the remaining green solvent mixture, to form the reaction solution.

FIGS. 1-7 identify various illustrative charts and graphs representing the results of synthesizing semicarbazones using the process(es) discussed herein.

Although discussed herein with respect to synthesizing imines, imine-related and imine-derived compounds generally, it is understood that each distinct compound identified herein, as well as other chemically similar compounds, may be synthesized using the processes discussed herein.

That is, the processes discussed herein with respect to synthesizing imines, imine-related and imine-derived compounds may be used specifically to synthesize oximes, omines, enamines, hydrazones (e.g., phenylhydrazones), semicarbazones, azines, quinoxalines, and quinoxalinones.

In some embodiments, the present disclosure includes a method of forming an imine, imine-related or imine-derived compound product, including the steps of: mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.) to form a mixture, wherein the green solvent includes an aqueous solution of dimethyl isosorbide or an aqueous solution of ethyl lactate; stirring the mixture for a first duration; and forming an imine, imine-related or imine-derived compound product. In embodiments, the first reactant is one or more of an aldehyde, ketone, or ester. In embodiments, the second reactant is further characterized as a nucleophilic/nitrogen-containing reactant. In embodiments, the imine-related compound is one or more of oxime, azine, hydrazone, phenylhydrazone, or semicarbazones. In embodiments, the first reactant is an ester and the compound product is characterized as quinoxalinone. In embodiments, the green solvent includes an aqueous solution of ethyl lactate over a range of concentration ratios from 60:40 to 100:0, 70:30 to 90:10, or 75:25 to 85:15 of ethyl lactate:water. In embodiments, the green solvent includes an aqueous solution of ethyl lactate at a concentration ratio of 80:20 ethyl lactate:water. In embodiments, the green solvent includes an aqueous solution of dimethyl isosorbide over a range of concentration ratios from 85:15 to 100:0, 90:10 to 95:5, or 92:8 of dimethyl isosorbide:water. In embodiments, the green solvent includes an aqueous solution of ethyl lactate over a range of concentration ratios from 60:40 to 100:0, 70:30 to 90:10, or 75:25 to 85:15 of ethyl lactate: lactic whey. In embodiments, the lactic whey is acidic whey. In embodiments, the method includes the the steps of: mixing the first reactant into solution in the green solvent to form a green solvent aldehyde solution, wherein the first reactant is an aldehyde reactant; mixing the second reactant into solution in water to form an aqueous nucleophilic/nitrogen-containing solution, wherein the second reactant is a nucleophilic/nitrogen containing reactant; mixing the green solvent aldehyde solution with the aqueous nucleophilic/nitrogen-containing solution; stirring the green solvent aldehyde solution together with the aqueous nucleophilic/nitrogen-containing solution; and forming an imine, imine-related or imine-derived compound product. In embodiments, the first reactant is an aldehyde reactant including a substituted benzaldehyde. In embodiments, the second reactant is a nucleophilic/nitrogen-containing reactant comprising a semicarbazide hydrochloride. In embodiments, the method further includes the steps of: heating the green solvent to create a supersaturated green solvent aldehyde solution, wherein the first reactant is an aldehyde reactant. In embodiments, the first reactant is an aldehyde reactant and the second reactant is a nucleophilic/nitrogen-containing reactant, and wherein the method includes; heating the first reactant in an aqueous solution to form a supersaturated green solvent aldehyde solution; mixing the second reactant into the supersaturated green solvent aldehyde solution within zero (0) to thirty (30) seconds after the first reactant is totally dissolved and completely enters solution in the green solvent. In embodiments, the method includes the steps of: cooling the aqueous nitrogen-containing reactant to between twenty degrees Celsius (20° C.) and negative twenty degrees Celsius (−20° C.) prior to mixing the green solvent solution with the aqueous nitrogen-containing solution. In embodiments, the method includes cooling the mixture. In embodiments, the method includes the steps of: mixing water together with the mixture of the green solvent. In embodiments, the method includes mixing a saturated brine together with the mixture of the green solvent. In embodiments, the brine further includes a supersaturated brine and is brought to a temperature within a range of between negative twenty degrees Celsius (−20° C.) and positive twenty degrees Celsius (20° C.). In embodiments, the method includes mixing a chilled saturated brine together with the mixture of the green solvent; and cooling the mixture of the green solvent. In embodiments, the method includes mixing a saturated brine together with the aqueous nitrogen-containing solution; and cooling a combined saturated brine and aqueous nitrogen-containing solution to between twenty degrees Celsius (20 C) and negative twenty degrees Celsius (−20 C) prior to mixing the green solvent aldehyde solution with the aqueous nucleophilic/nitrogen-containing solution. In embodiments, the method includes a compound product characterized as an enamine compound, wherein the first reactant includes a ketone or aldehyde with at least one hydrogen atom attached to an alpha-carbon relative to the carbonyl group or a 1,3-dicarbonyl compound such as 2,4-pentanedione, and wherein the second reactant is characterized as a secondary amine or an aromatic amine or a substituted aromatic amine.

In embodiments, the present disclosure includes a method of forming an imine, imine-related or imine-derived compound product, including the steps of: mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.), wherein the green solvent includes an aqueous solution of ethyl lactate and lactic whey; stirring the mixture for a first duration; and forming an imine, imine-related or imine-derived compound product. In embodiments, the lactic whey is acidic whey. In embodiments, the green solvent includes an aqueous solution of ethyl lactate over a range of concentration ratios from 70:30 to 90:10, or 75:25 to 85:15 of ethyl lactate:lactic whey.

In embodiments, the present disclosure includes a solvent solution suitable for forming an imine, imine-related or imine-derived compound, or pharmaceutically acceptable salt thereof, including: an aqueous solution of ethyl lactate and lactic whey. In embodiments, the aqueous solution includes ethyl lactate over a range of concentration ratios from 70:30 to 90:10, or 75:25 to 85:15 of ethyl lactate:lactic whey. In embodiments, the lactic whey is acidic whey or sweet whey.

Various example processes and data relating to synthesizing distinct compounds are provided below, with accompanied figures.

Example 1

Figure 8:
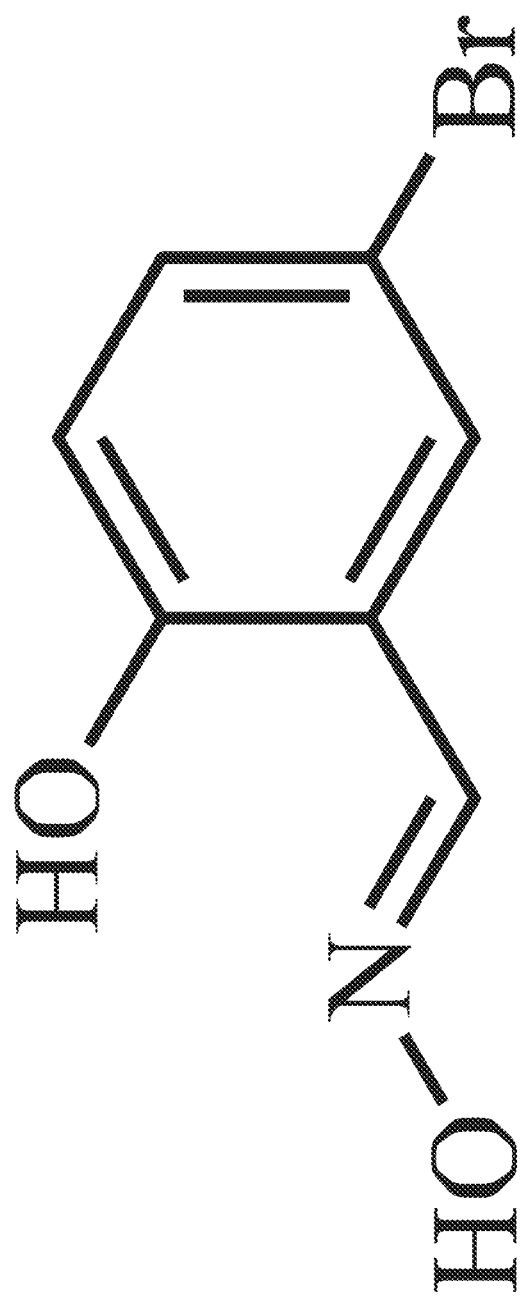
FIG. 8 depicts the formulation for 3-hydroxybenzaldehyde oxime.
Figure 9A:
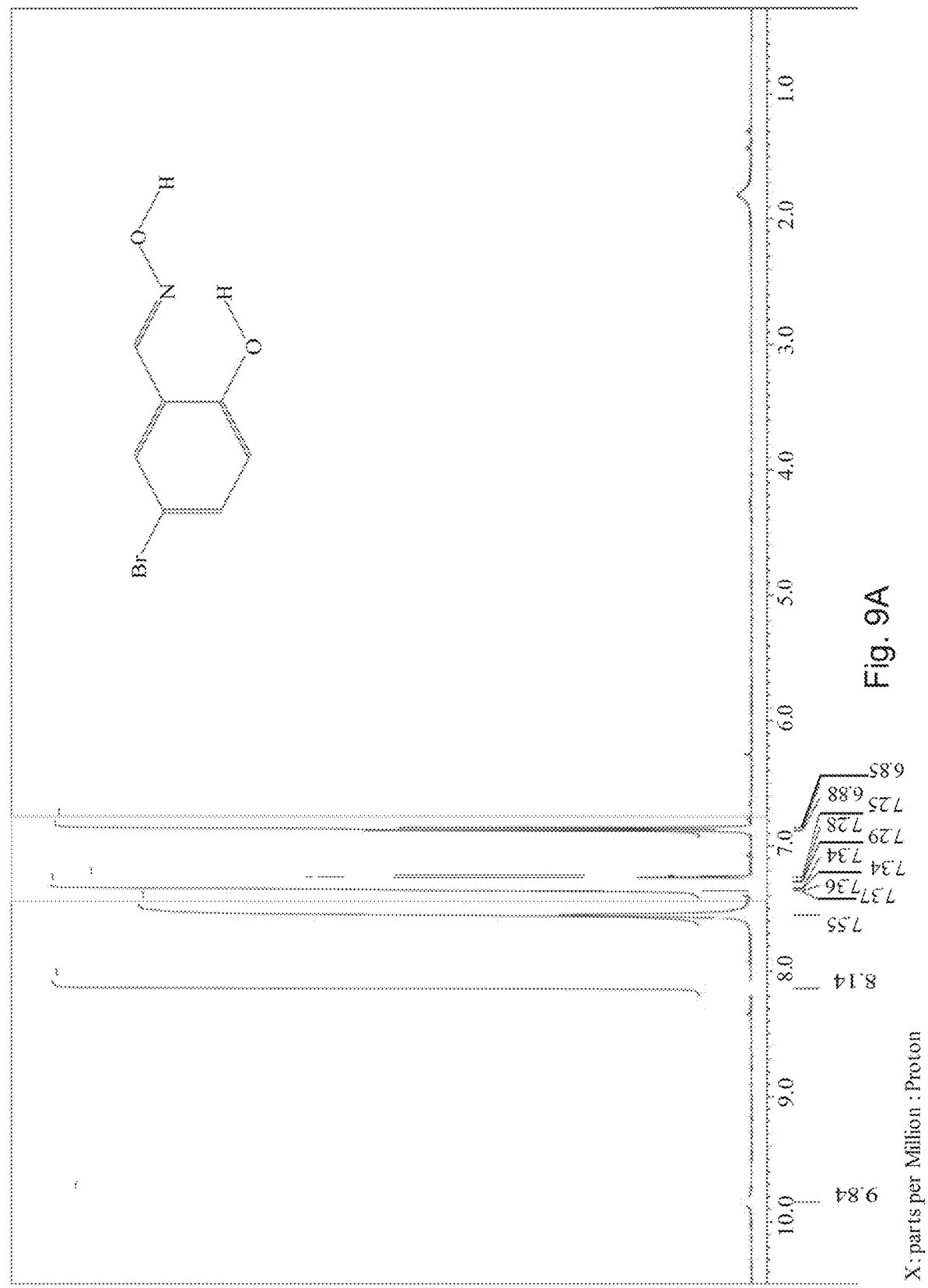
FIGS. 9A and 9B depict the $^1$H NMR spectrum of 5-bromosalicylaldehyde oxime ($CDCl_3$, 400 MHz).
Figure 9B:
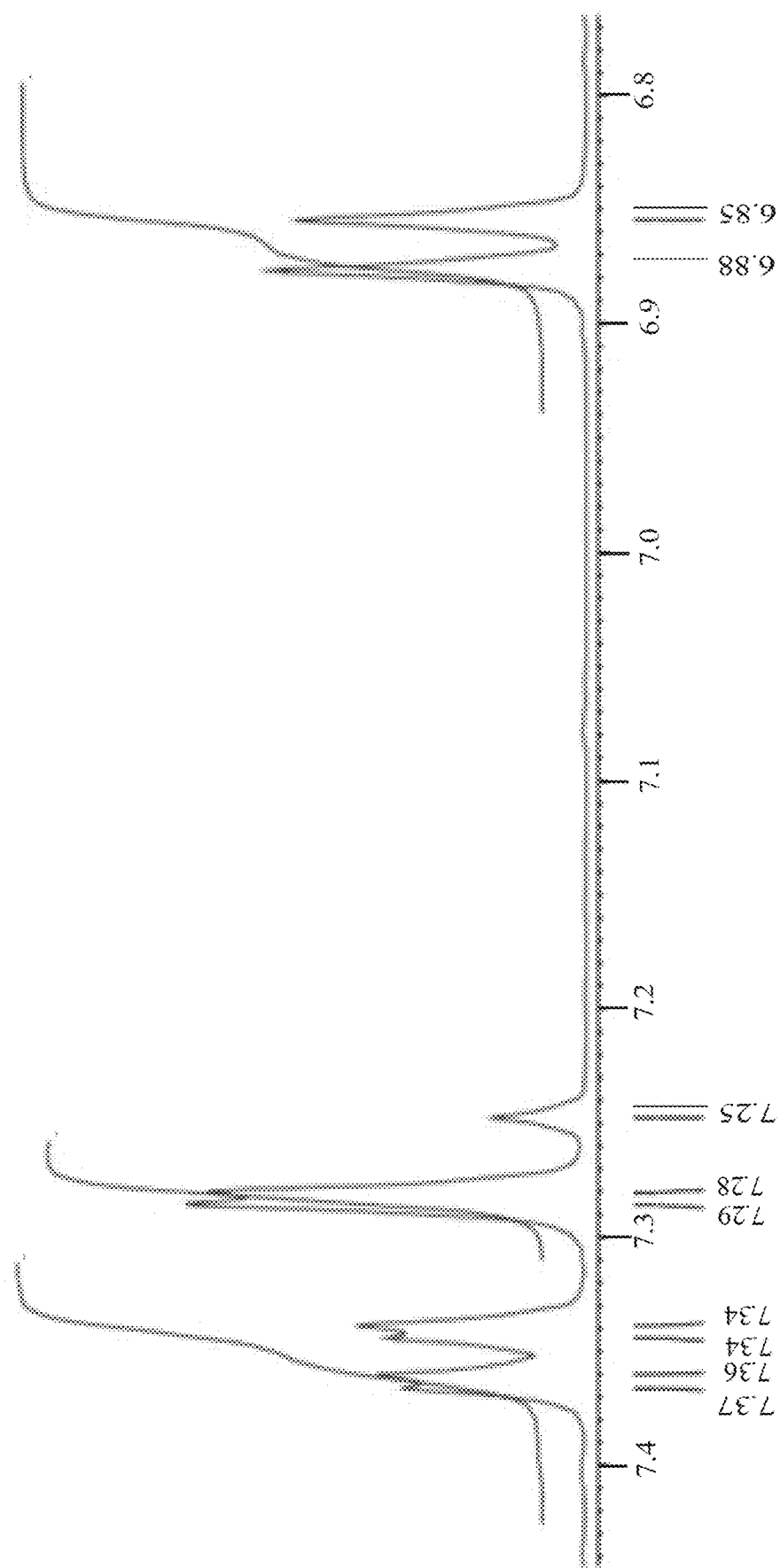

5-Bromosalicylaldehyde Oxime—FIGS. 8 and 9

A solvent mixture was prepared as with 20 mL ethyl lactate, and 5 mL water. To a beaker containing 10 mmol 5-bromosalicylaldehyde, 23 mL of the solvent was added with gentle heat used to dissolve the solid. The solution was allowed to cool to room temperature. To a separate beaker was added 15 mmol of hydroxylamine (50% solution in water) with 1 mL of the solvent. The two solutions were combined, the remaining solvent used to rinse the empty beaker, and the rinse added to the reaction solution. The reaction solution was allowed to sit undisturbed at room temperature for 30 minutes, then transferred to an ice bath. An additional 50 mL ice-cold water was added. Once crystallization was complete (~12 min), the product was vacuum filtered, rinsed with ice-cold water, and air dried overnight.

$^1$H-NMR (400 MHz, CHLOROFORM-D) δ9.84 (s, 1H), 8.14 (s, 1H), 7.55 (s, 1H), 7.35 (dd, J=8.8, 2.3 Hz, 1H), 7.28 (d, J=2.1 Hz, 1H), 6.87 (d, J=8.8 Hz, 1H)

$^{13}$C-NMR (101 MHz, CHLOROFORM-D) δ 156.4, 152.0, 134.1, 132.9, 118.7, 118.1, 111.5

DEPT-135 NMR (101 MHz, CHLOROFORM-D) δ 152.0, 134.1, 132.9, 118.7

| Reaction Time | mp (° C.) | Yield | Purity ($^1$H NMR) | Pure Yield |
|---|---|---|---|---|
| 42 min | 126.3-127.3 Not recrystallized | 74.29% | 98.93% 0.77% $H_2O$, 0.23% EL, 0.07% HA | 73.50% |

Example 2

Figure 10:
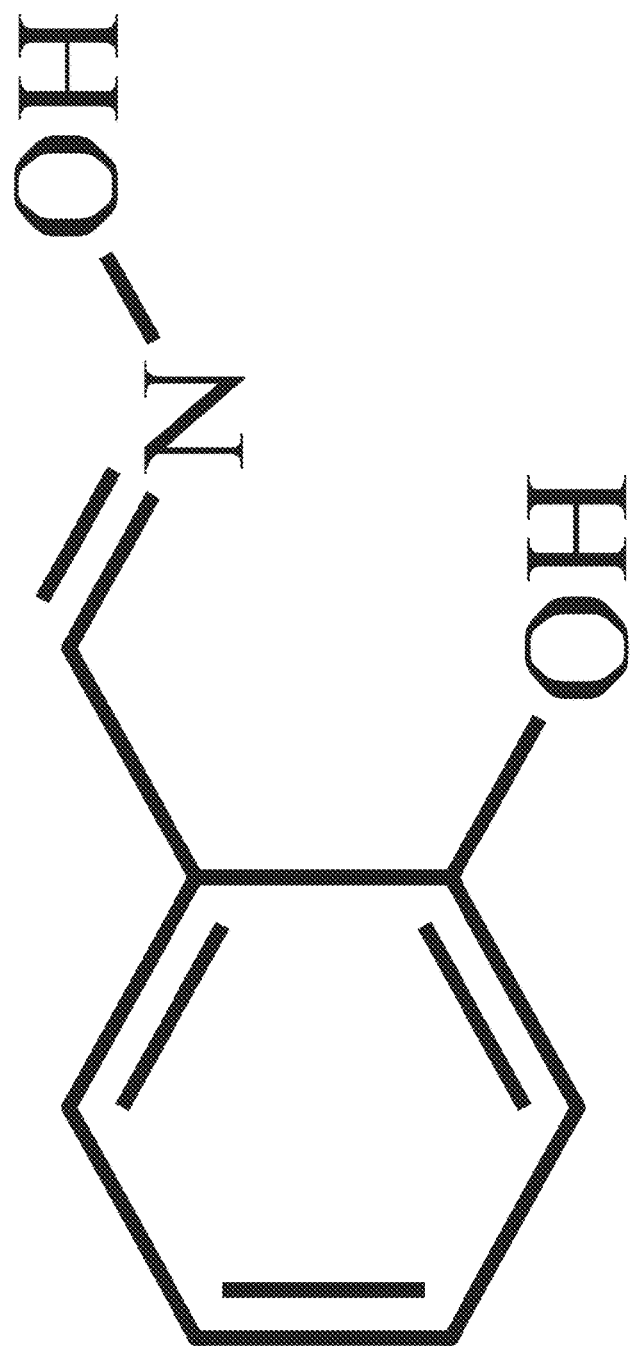
FIG. 10 depicts salicylaldehyde oxime.
Figure 11A:
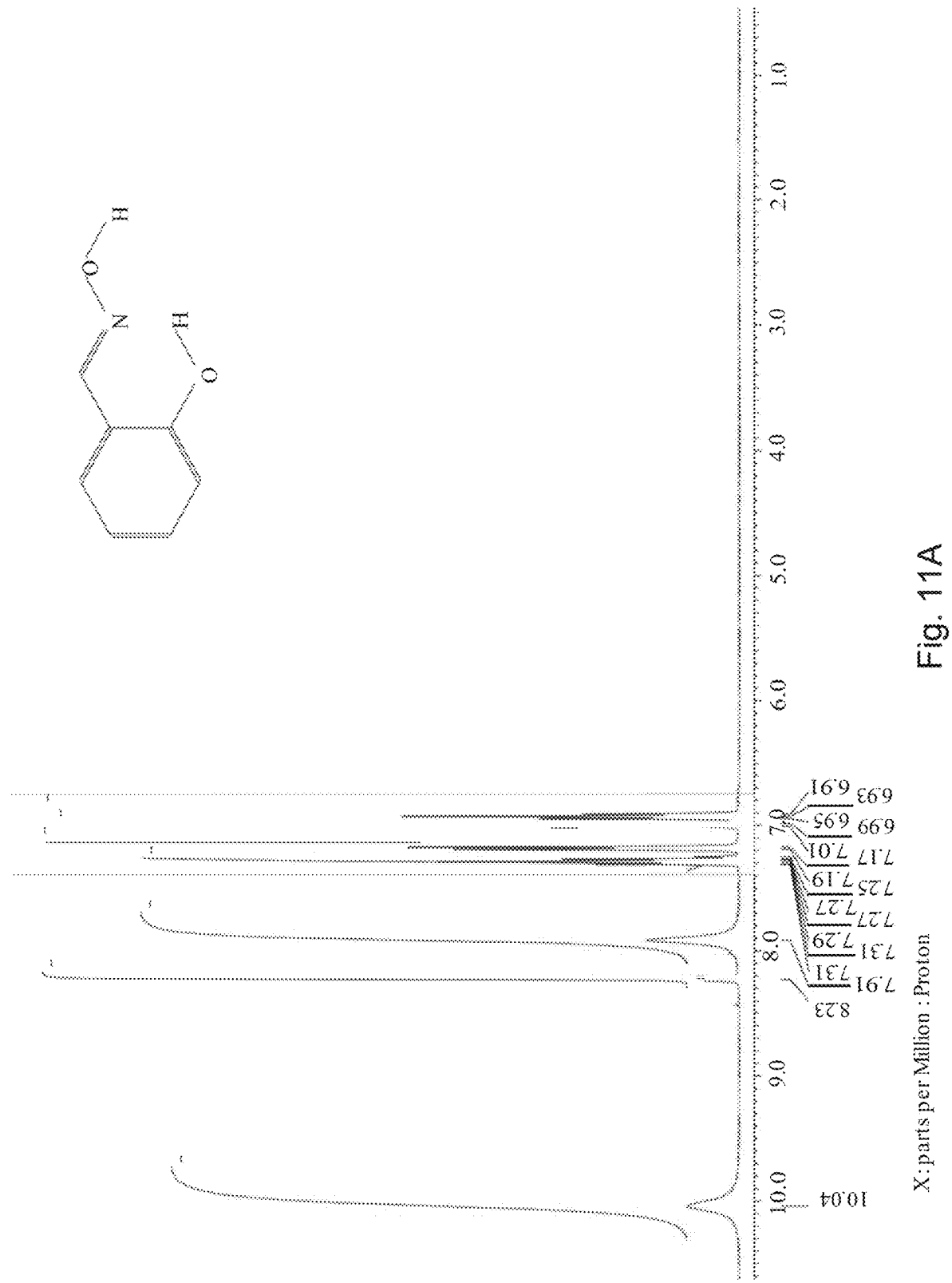
FIGS. 11A and 11B depict the $^1$H NMR spectrum of salicylaldehyde oxime ($CDCl_3$, 400 MHz).
Figure 11B:
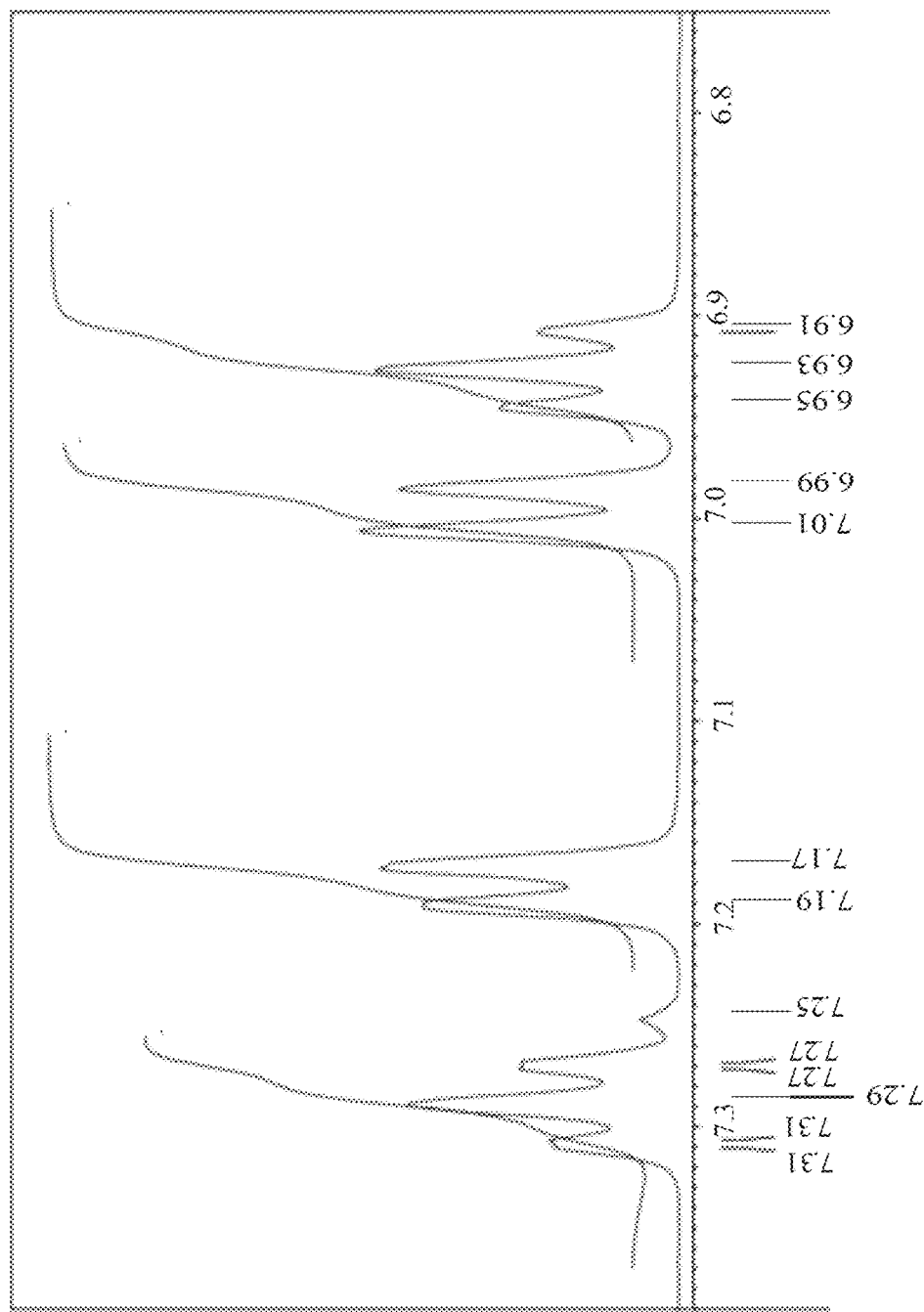

Salicylaldehyde Oxime—FIGS. 10 and 11A and 11B

A solvent mixture was prepared as with 4 mL ethyl lactate and 1 mL water. To a beaker containing 10 mmol salicylaldehyde, 1 mL of the solvent was added. To a separate beaker was added 15 mmol of hydroxylamine (50% solution in water) with 3 mL of the solvent. The two solutions were combined, the remaining solvent used to rinse the empty beaker, and the rinse added to the reaction solution. The reaction solution was allowed to sit undisturbed at room temperature for 5 minutes, then transferred to an ice bath. Once crystallization was complete, the product was vacuum filtered, rinsed with ice-cold water, and air dried overnight.

$^1$H-NMR (400 MHz, CHLOROFORM-D) δ 10.04 (s, 1H), 8.23 (s, 1H), 7.91 (s, 1H), 7.31-7.27 (m, 1H), 7.18 (d, J=7.6 Hz, 1H), 7.00 (d, J=8.3 Hz, 1H), 6.93 (t, J=7.5 Hz, 1H)

$^{13}$C-NMR (101 MHz, CHLOROFORM-D) δ 157.1, 153.1, 131.4, 130.9, 120.0, 116.8, 116.5

DEPT-135 NMR (101 MHz, CHLOROFORM-D) δ 153.1, 131.4, 130.9, 120.0, 116.8

| Reaction Time | mp (° C.) | Yield | Purity ($^1$H NMR) | Pure Yield |
|---|---|---|---|---|
| 15 min | 55.6-57.1 Not recrystallized | 74.03% | 99.57% 0.29% $H_2O$, 0.05% EL, 0.09% HA | 73.71% |

Example 3

Figure 12:
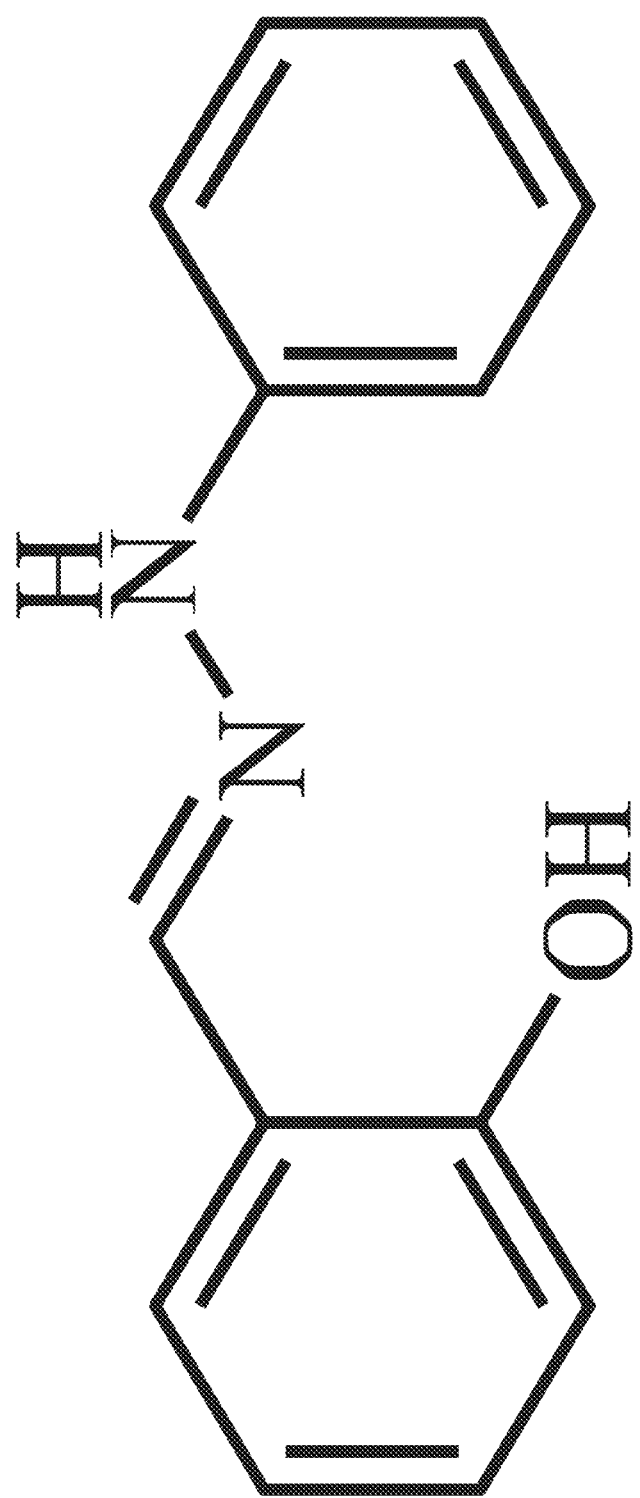
FIG. 12 depicts salicylaldehyde phenylhydrazone.
Figure 13A:
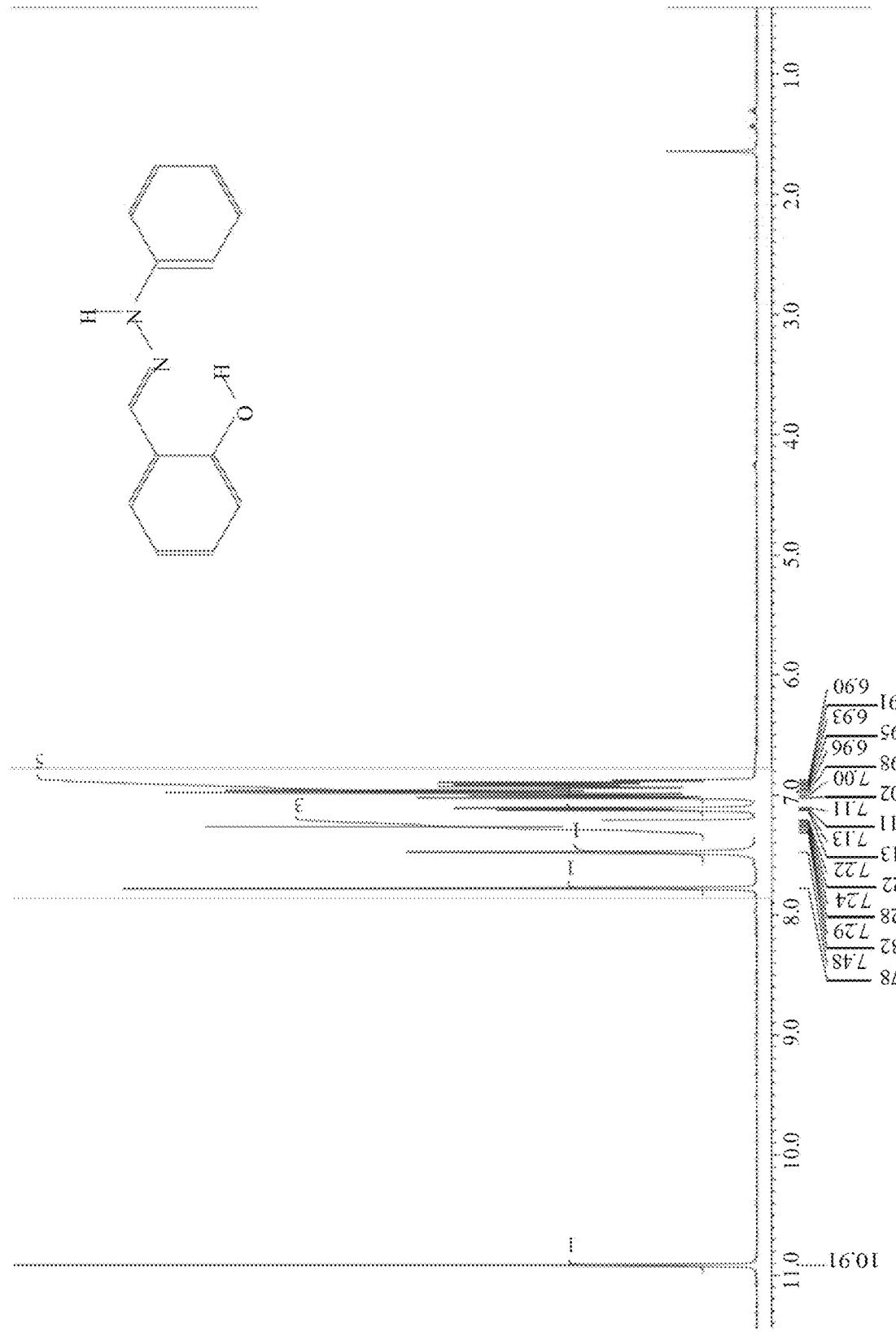

Salicylaldehyde Phenylhydrazone—FIGS. 12 and 13A and 13B

A solvent mixture was prepared with 4 mL ethyl lactate and 1 mL water. To a beaker containing 10 mmol salicylaldehyde, 2 mL of the solvent was added. To a separate beaker was added 10 mmol phenylhydrazine with 2 mL of the solvent. The two solutions were combined, the remaining solvent used to rinse the empty beaker, and the rinse added to the reaction solution. The reaction solution was allowed to sit undisturbed at room temperature for 15 s for crystallization to complete, then transferred to an ice bath. The product was vacuum filtered, rinsed with ice-cold water, and air dried overnight.

$^1$H-NMR (400 MHz, CHLOROFORM-D) δ 10.91 (s, 1H), 7.78 (s, 1H), 7.48 (s, 1H), 7.32-7.22 (m, 3H), 7.12 (dd, J=7.6, 0.9 Hz, 1H), 7.02-6.88 (m, 5H) $^{13}$C-NMR (101 MHz, CHLOROFORM-D) δ 157.1, 143.5, 141.3, 130.1, 129.7, 129.5, 121.0, 119.6, 118.6, 116.7, 112.7 DEPT-135 NMR (101 MHz, CHLOROFORM-D) 6141.3, 130.1, 129.7, 129.5, 121.0, 119.6, 116.7, 112.7

| Reaction Time | mp (° C.) | Yield | Purity ($^1$H NMR) | Pure Yield |
|---|---|---|---|---|
| 15 s | 144.0-144.7 Not recrystallized | 98.78% | 99.11% 0.56% H$_2$O, 0.33% EL | 97.90% |

Example 4

Figure 14:
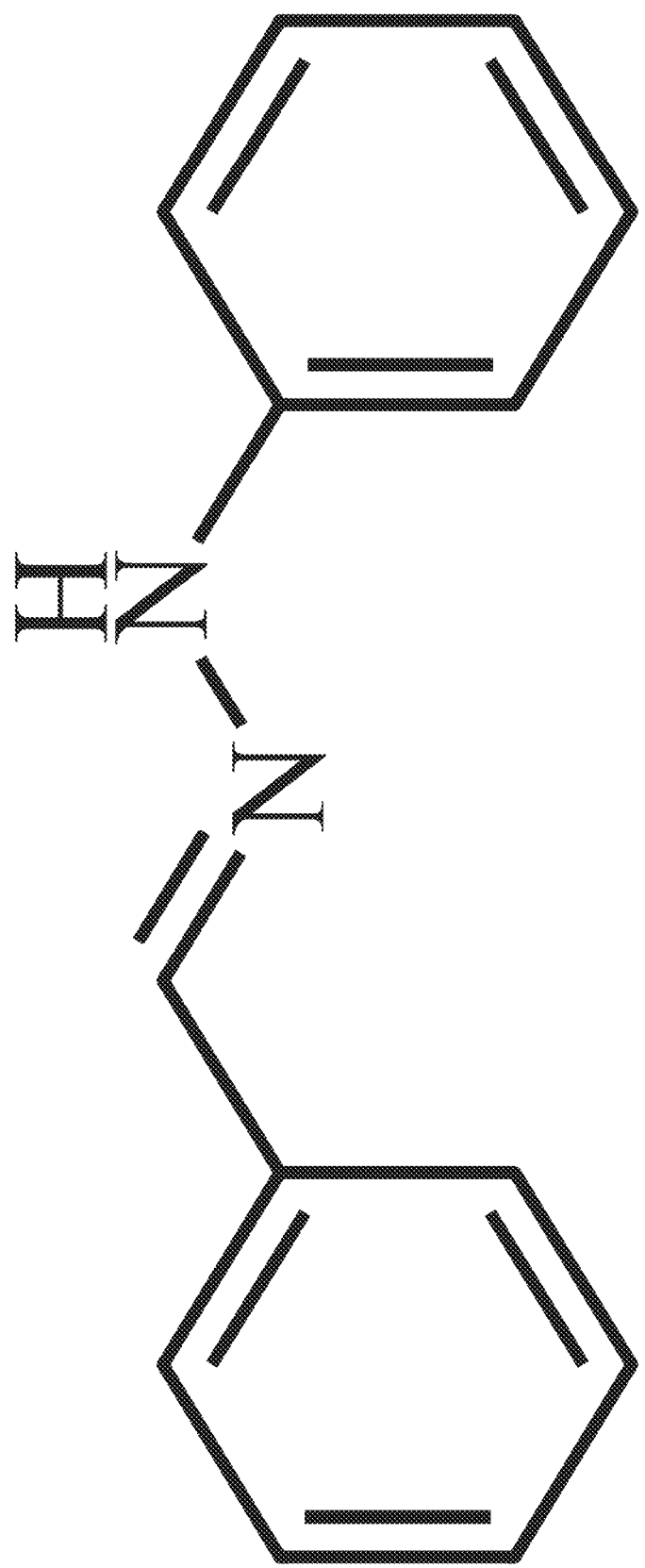
FIG. 14 depicts benzaldehyde phenylhydrazone.
Figure 15A:
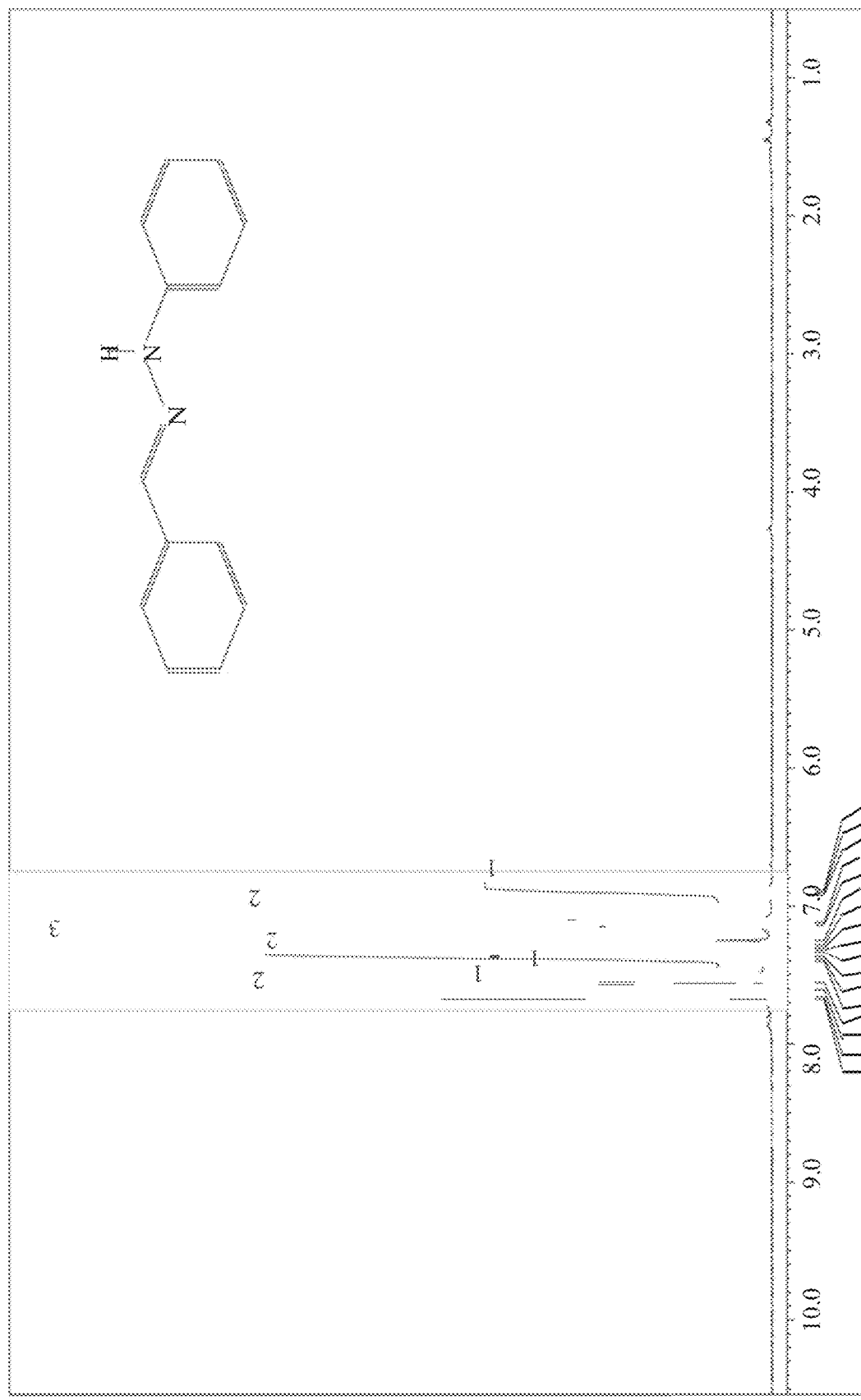
FIGS. 15A and 15B depict the 1H NMR spectrum of benzaldehyde phenylhydrazone ($CDCl_3$, 400 MHz).
Figure 15B:
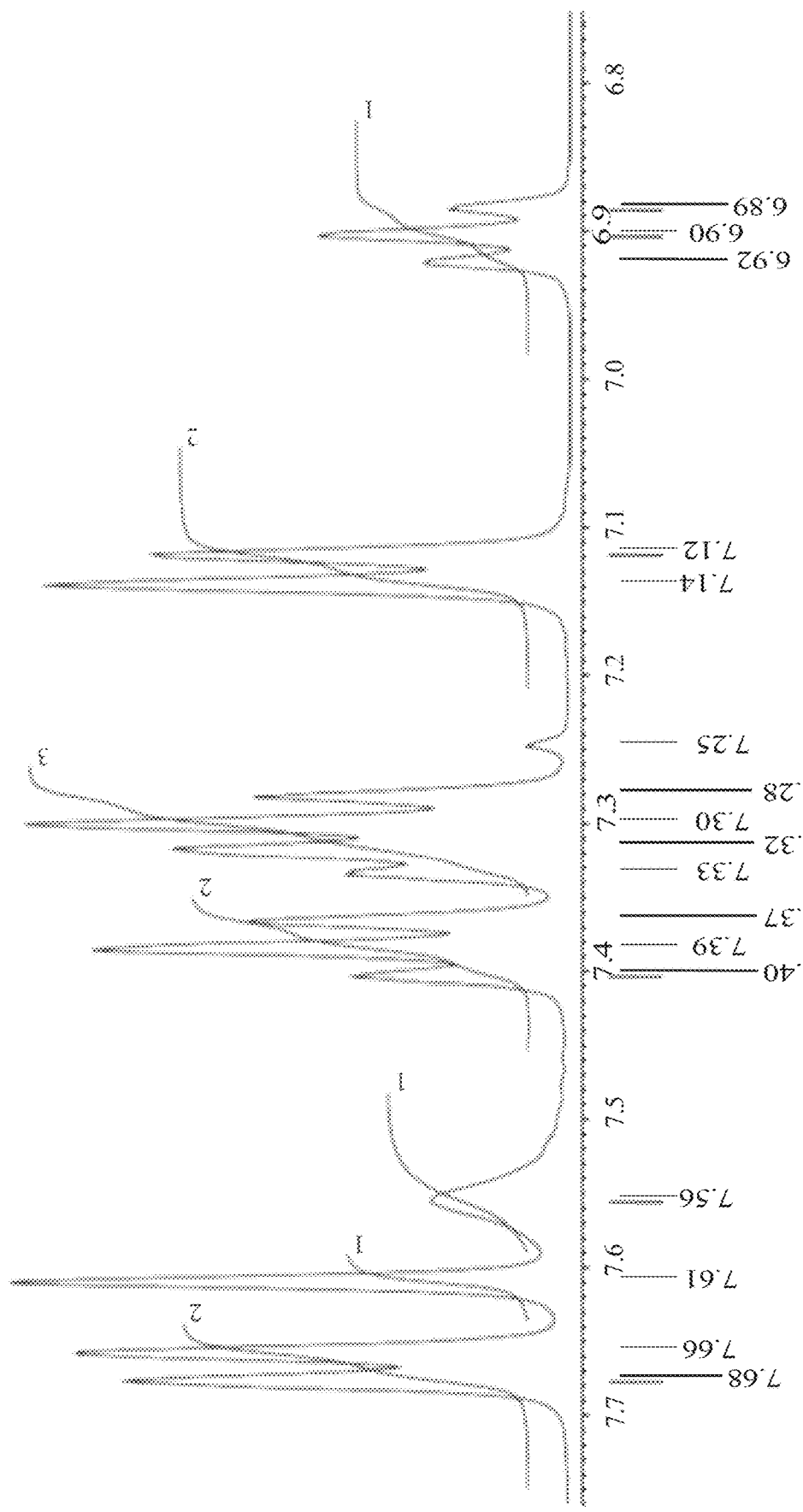

Benzaldehyde Phenylhydrazone—FIGS. 14 and 15A and 15B

A solvent mixture was prepared with 4.5 mL ethyl lactate and 0.5 mL water. To a beaker containing 10 mmol salicylaldehyde, 1.5 mL of the solvent was added. To a separate beaker was added 10 mmol phenylhydrazine with 1.5 mL of the solvent. The two solutions were combined, the remaining solvent used to rinse the empty beaker, and the rinse added to the reaction solution. The reaction solution was allowed to sit undisturbed at room temperature for 5 s for crystallization to complete, then transferred to an ice bath. The product was vacuum filtered, rinsed with ice-cold water, and air dried overnight.

$^1$H-NMR (400 MHz, CHLOROFORM-D) δ 7.67 (d, J=7.6 Hz, 2H), 7.61 (s, 1H), 7.56 (s, 1H), 7.39 (t, J=7.3 Hz, 2H), 7.33-7.28 (m, 3H), 7.13 (d, J=8.6 Hz, 2H), 6.90 (t, J=7.2 Hz, 1H)

$^{13}$C-NMR (101 MHz, CHLOROFORM-D) δ 144.8, 137.4, 135.4, 129.5, 128.7, 128.6, 126.3, 120.2, 112.9

DEPT-135 NMR (101 MHz, CHLOROFORM-D) δ 137.4, 129.5, 128.7 128.6 126.3 120.2 112.9

| Reaction Time | mp (° C.) | Yield | Purity ($^1$H NMR) | Pure Yield |
|---|---|---|---|---|
| 5 s | 150.9-155.8 (dec Not recrystallized | 96.16% | 99.47% 0.09% H$_2$O, 0.34% EL, 0.05% benzaldehyde, 0.05% phenylhydrazine | 95.64% |

Example 5

Figure 16:
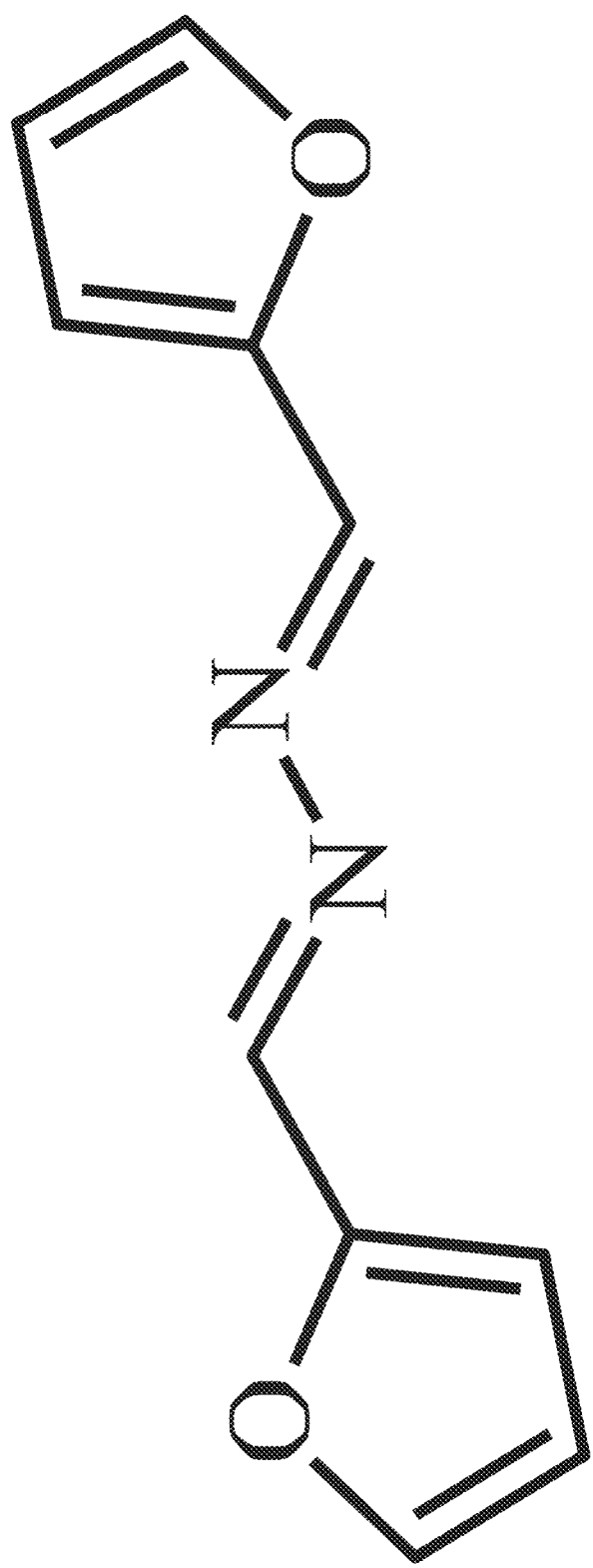
FIG. 16 depicts furaldehyde azine.
Figure 17A:
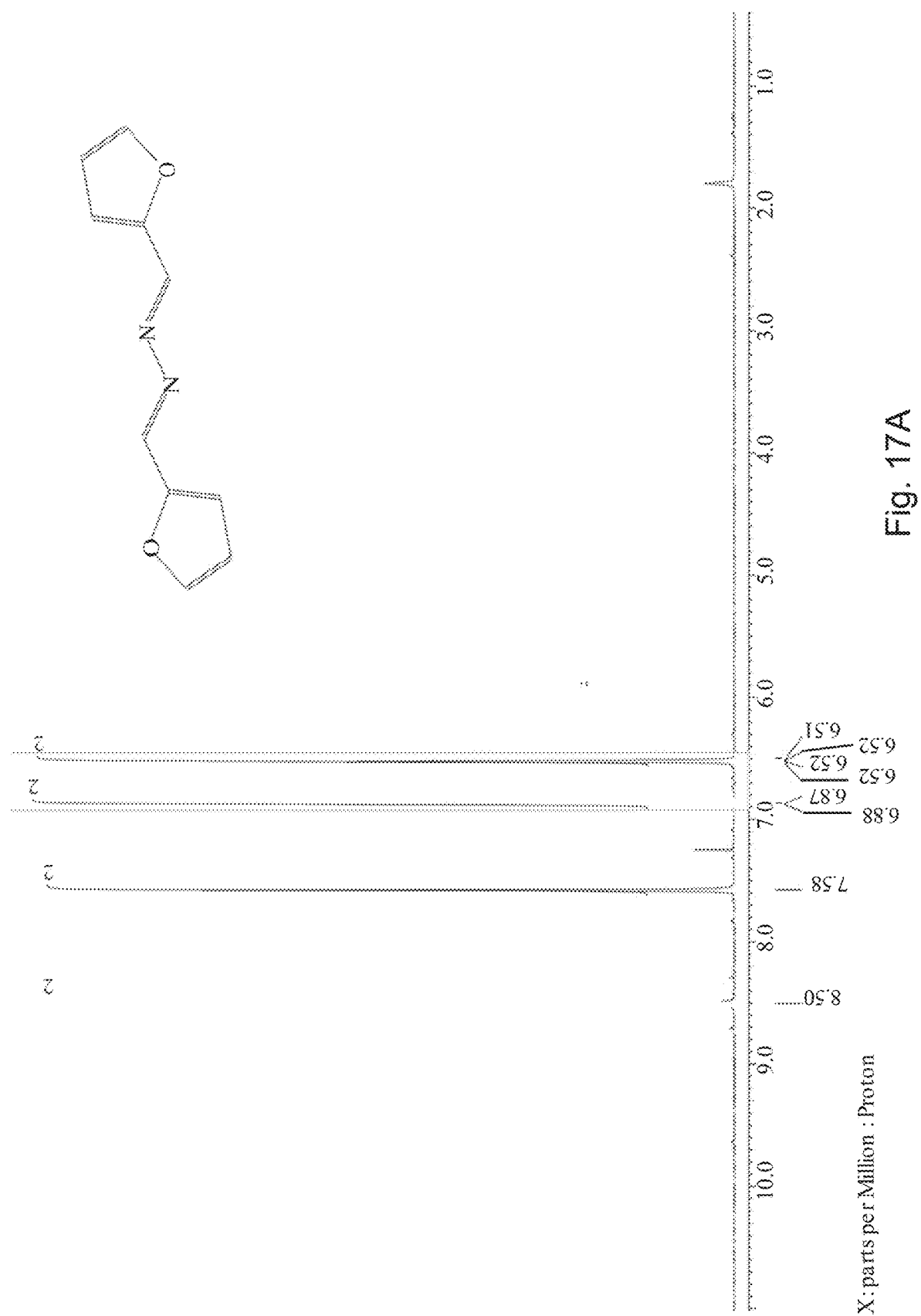

2-Furaldehyde Azine—FIGS. 16 and 17A and 17B

A solvent mixture was prepared with 3.5 mL ethyl lactate and 1.5 mL water. To a beaker containing 10 mmol salicylaldehyde, 1.5 mL of the solvent was added. To a separate beaker was added 5 mmol hydrazine (64% in water) with 1.5 mL of the solvent. The two solutions were combined, the remaining solvent used to rinse the empty beaker, and the rinse added to the reaction solution. The reaction solution was allowed to sit undisturbed at room temperature for 2 minutes, then transferred to an ice bath min for crystallization to complete for another 3 minutes. The product was vacuum filtered, rinsed ice-cold water, and air dried overnight.

$^1$H-NMR (400 MHz, CHLOROFORM-D) δ 8.50 (s, 2H), 7.58 (s, 2H), 6.87 (d, J=3.1 Hz, 2H), 6.52 (dd, J=3.2, 1.7 Hz, 2H)

$^{13}$C-NMR (101 MHz, CHLOROFORM-D) δ 151.1, 149.5, 145.9, 117.0, 112.4

DEPT-135 NMR (101 MHz, CHLOROFORM-D) δ 151.1, 145.9, 117.0, 112.4

| Reaction Time | mp (° C.) | Yield | Purity ($^1$H NMR) | Pure Yield |
|---|---|---|---|---|
| 5 min | 101.2-104.9 color change/dec Not recrystallized | 74.50% | 98.44% 0.31% 2-furaldehyde, 0.26% EL, 0.96% H$_2$O | 73.33% |

Example 6

Figure 18:
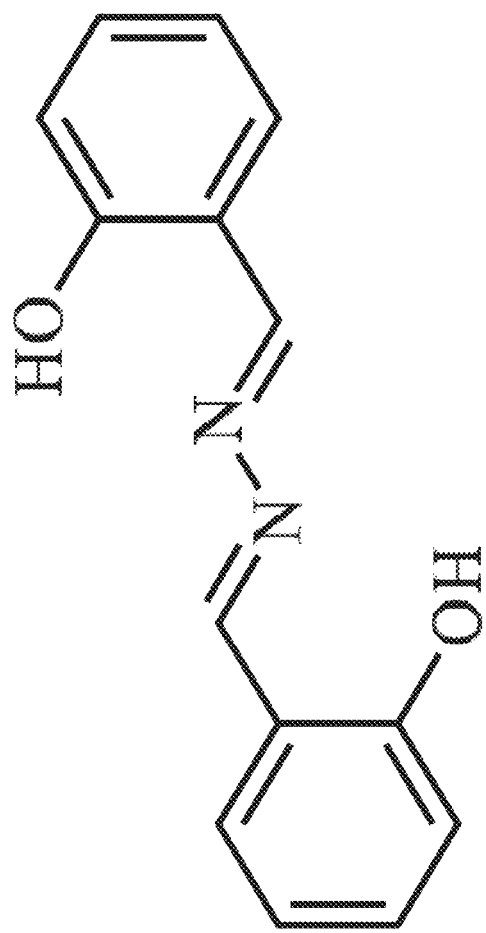
FIG. 18 depicts salicylaldehyde azine.
Figure 19A:
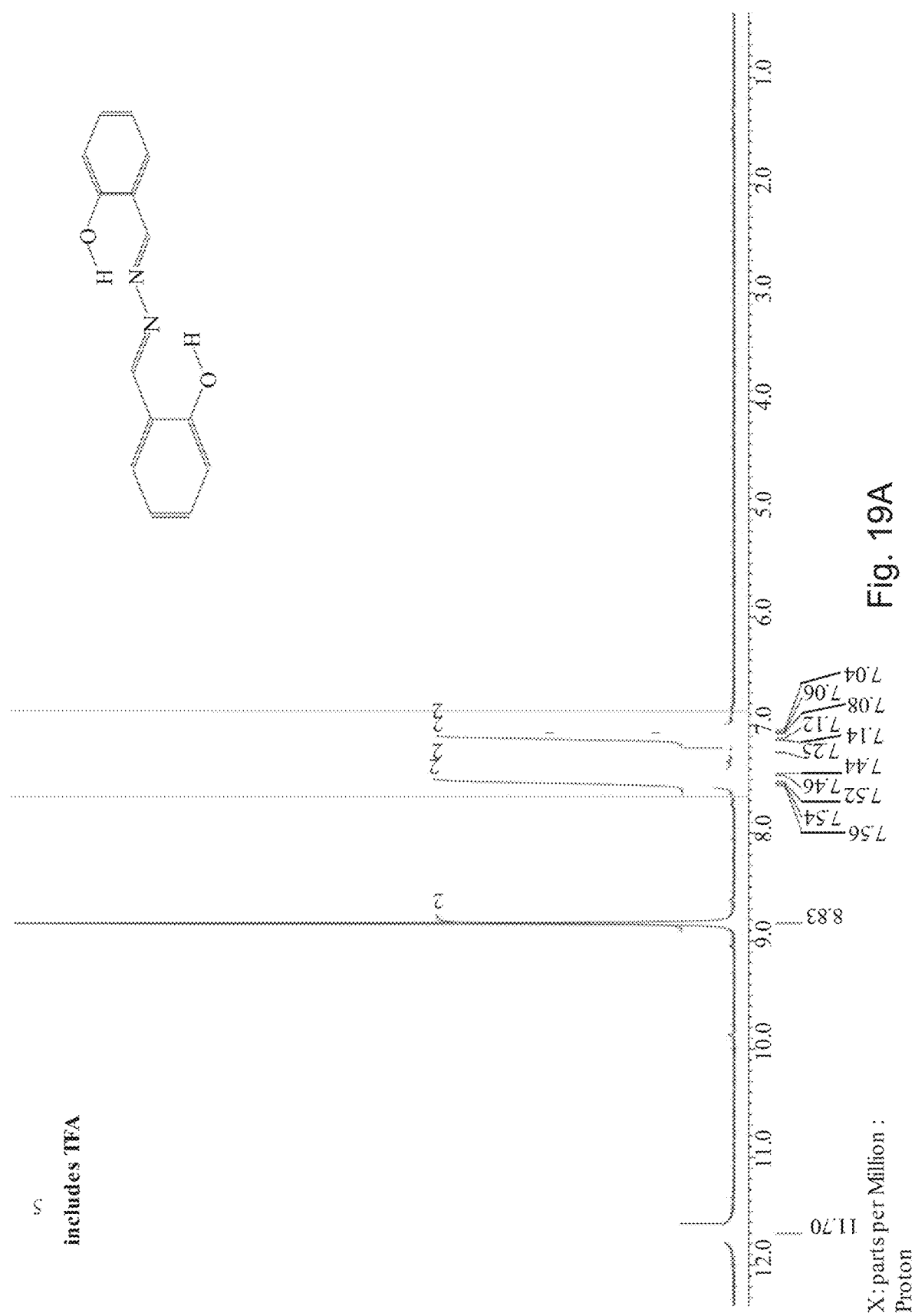
FIGS. 19A and 19B depict the $^1$H NMR spectrum of salicylaldehyde azine ($CDCl_3$ with TFA for solubility, 400 MHz).
Figure 19B:
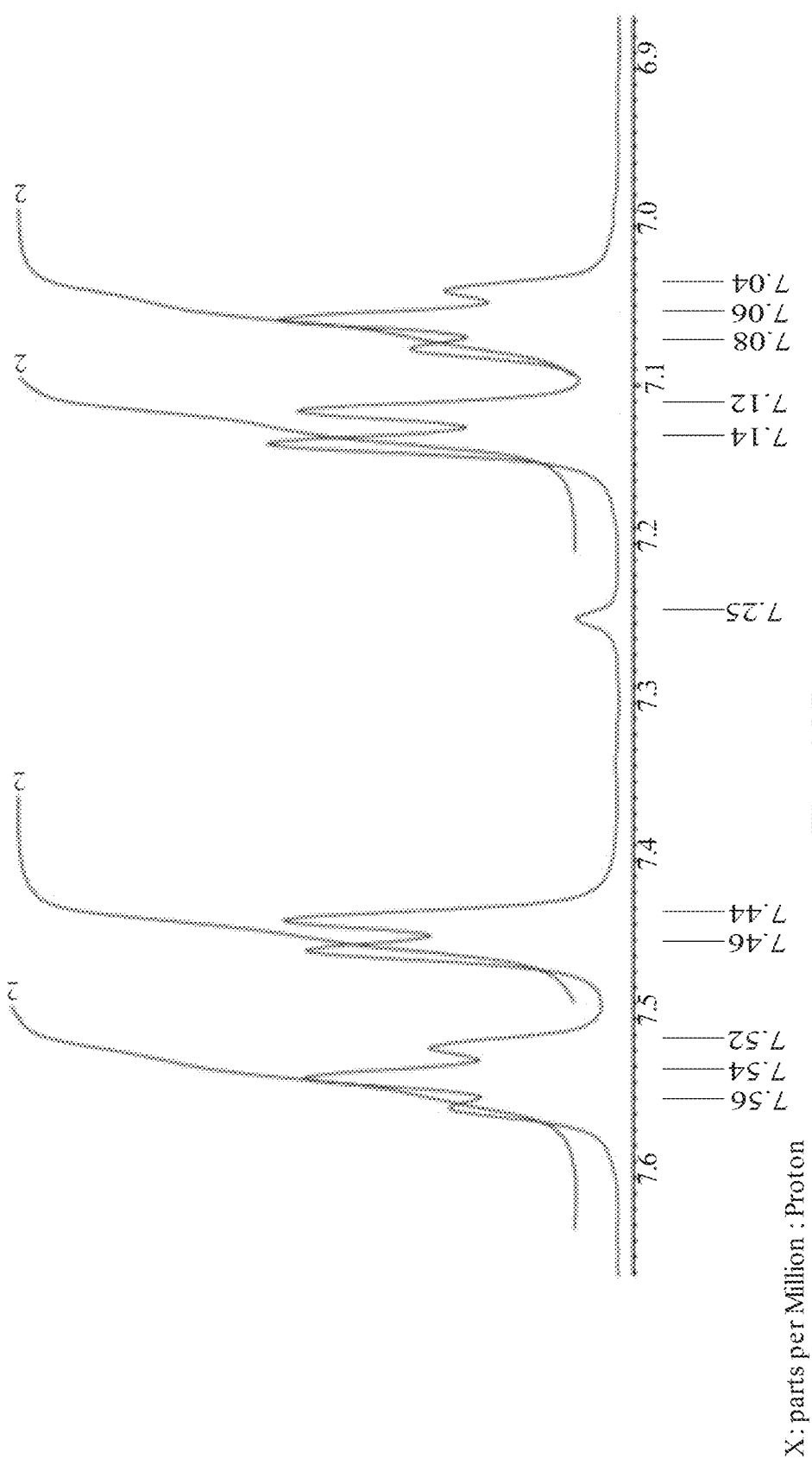
Figure 20A:
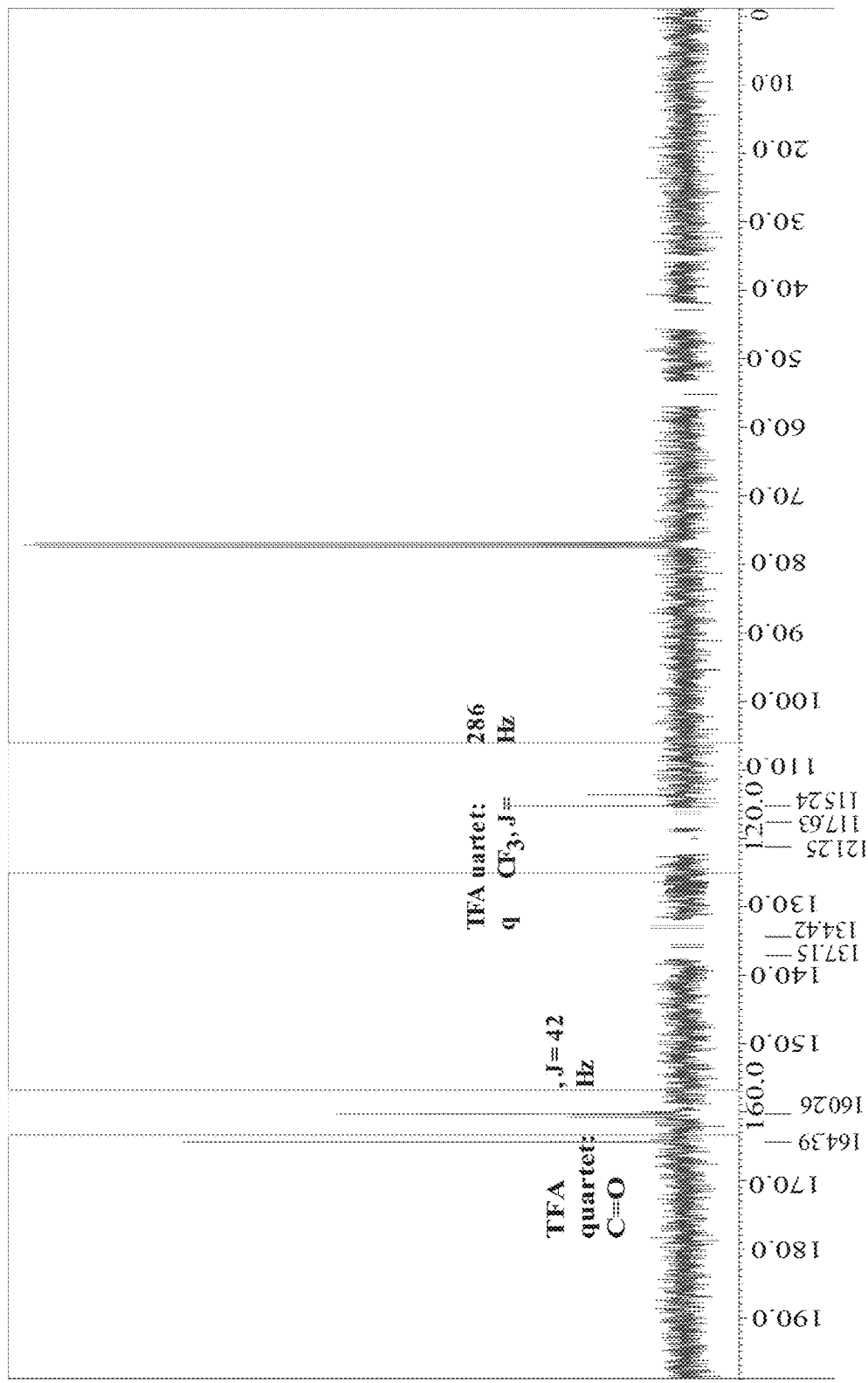
Figure 20C:
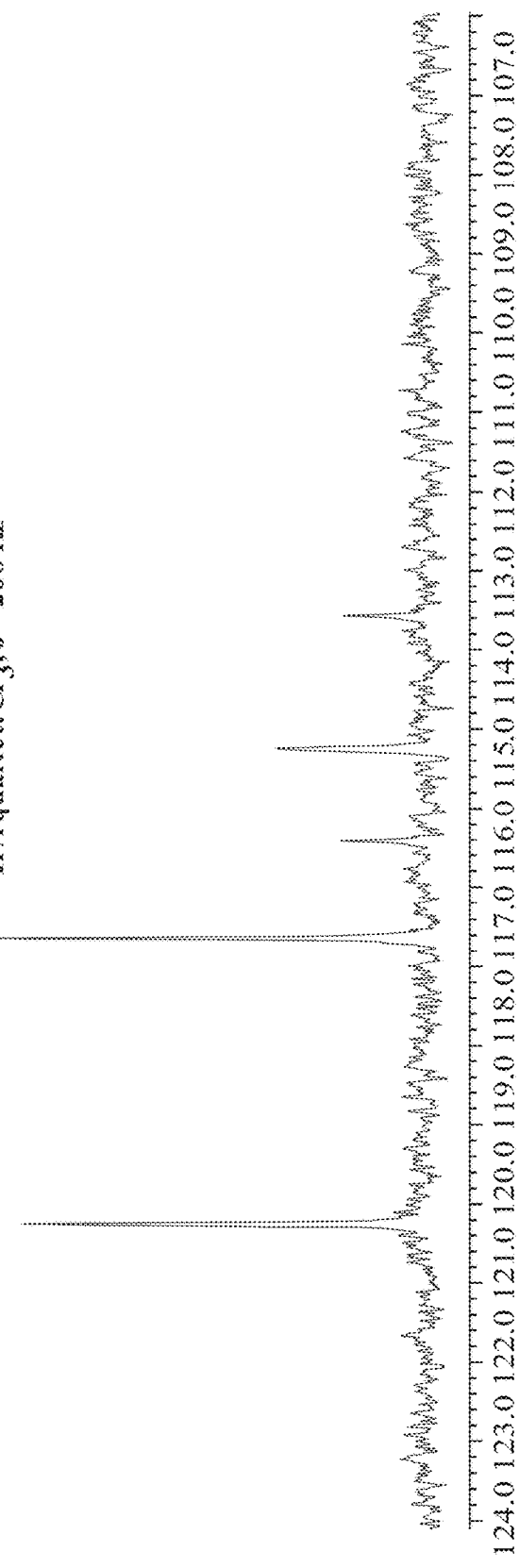

Salicylaldehyde Azine—FIGS. 18-20

A solvent mixture was prepared with 9 mL ethyl lactate and 1 mL water. To a beaker containing 10 mmol salicylaldehyde, 3 mL of the solvent was added. To a separate beaker was added 5 mmol hydrazine (64% in water) with 3 mL of the solvent. The two solutions were combined, the remaining solvent used to rinse the empty beaker, and the rinse added to the reaction solution. The reaction solution was allowed to sit undisturbed at room temperature for 2 min for crystallization to complete, then transferred to an ice bath. The product was vacuum filtered, rinsed with ice-cold water, and air dried overnight.

$^1$H-NMR (400 MHz, CHLOROFORM-D+TFA) δ 11.70 (s, 2H), 8.83 (s, 2H), 7.54 (t, J=7.5 Hz, 2H), 7.45 (d, J=7.3 Hz, 2H), 7.13 (d, J=8.3 Hz, 2H), 7.06 (t, J=7.3 Hz, 2H); trifluoroacetic acid (TFA) overlaps with the signal at 11.70 ppm $^{13}$C-NMR (101 MHz, CHLOROFORM-D with TFA) δ 164.4, 160.3, 137.2, 134.4, 121.3, 117.6, 115.2

DEPT-135 NMR (101 MHz, CHLOROFORM-D) δ 164.4, 137.2, 134.5, 121.3, 117.7

| Reaction Time | mp (° C.) | Yield | Purity ($^1$H NMR) | Pure Yield |
|---|---|---|---|---|
| 2 min | 217.3-217.8 Not recrystallized | 73.41% | 99.11% 0.81% salicylaldehyde, 0.09% EL | 72.75% |

Examples 7 and 8

Quinoxaline and Quinoxalinone

With respect to the formation of Quinoxaline or Quinoxalinone, ortho-phenylene diamine or 4-substituted ortho-phenylene diamine is dissolved in a solvent (e.g., Ethyl lactate or ethyl lactate:water mixtures to 80:20 ethyl lactate: water or dimethyl isosorbide or dimethyl isosorbide:water mixtures to 85:15 dimethyl isosorbide:water). For quinoxalines, benzil is dissolved in a similar solvent as the orthophenylene diamine. The diamine solution is mixed with the benzil solution and allowed to stand at room temperature until a precipitate is formed to give the 2,3-diphenylquinoxalines. For quinoxalinones, ethyl pyruvate is added without dissolving it in a solution. The diamine solution is mixed with ethyl pyruvate and allowed to stand at room temperature until a precipitate is formed to give the 3-methylquinoxalinones. In both quinoxaline and quinoxalinone, the solids are filtered off, washed with cold reaction solvent twice, with cold water twice, dried overnight in vacuo at room temperature, and finally assayed for structure/purity by NMR.

Additional Material

The focus of this research was to demonstrate the use of a green chemical synthesis in creating these molecules, ultimately optimizing a reaction process for mass-scale production. Green chemistry involves chemical research that is carried out with safe, environmentally friendly reagents in low-energy conditions. Using novel green solvents, an array of semicarbazones were synthesized in an efficient and eco-friendly matter, satisfying green chemistry requirements. The reaction was optimized using two solvents—ethyl lactate and dimethyl isosorbide—both of which qualify as green and are found in cosmetic products. In embodiments, these two sustainable solvents, it has been demonstrated that the reaction can produce yields of product at room temperature in minutes. These reactions can now be investigated for industrial scale-up, while other small-scale syntheses in these solvents are being developed. The results of this study have promising implications for the development of other green routes to molecules of industrial importance under efficient, environmentally friendly conditions. Moreover, it has been found that green solvents including lactic whey are useful in forming imine, imine-related, and imine derived chemicals of the present disclosure.

An array of semicarbazones were synthesized by the reaction of semicarbazide hydrochloride with substituted benzaldehydes. The reactions were performed in two different novel green solvents, ethyl lactate and dimethyl isosorbide. The yields and purities of each product were compared to determine the optimal solvent:water proportion. The products for each reaction were analyzed using $^1$H NMR spectroscopy as well as LC-MS. The results indicate that the reaction is most efficient when the ratio of ethyl lactate:water is 80:20, and the ratio of dimethyl isosorbide to water is 92:8. Generally the semicarbazones synthesized in ethyl lactate displayed a higher yield and degree of purity.

Semicarbazones are a class of organic molecules that are of growing interest due to their versatile use in industry, agriculture, and pharmaceuticals. The most promising aspect of semicarbazones is their use in medicine and body metabolism. Recent research into this group of imine derivatives has shown that they are the components of several useful pharmaceutical molecules, some of which have antibiotic, anticancer and anti-convulsant properties. Vanillin semicarbazone, analyzed in this study, is an example of an anti-cancer activity. This project was proposed to use semicarbazones as the building blocks for medicinal compounds, giving way to more practical implications for pharmaceutical research.

Perusal of literature has indicated that the most common syntheses of semicarbazones are done with reagents that are toxic and nonenvironmentally friendly. The method practiced here aims to provide an efficient synthesis that qualifies as green. Green chemistry is broadly defined as a research method in which work is carried out only with non-toxic, environmentally friendly reagents.

Developing a method to synthesize semicarbazones by green methods has several implications for further study. The synthesis proposed here is done on a microscale level, but promising results at this level will allow for industrial scale-up in the future. Because of their use as synthetic intermediates, large-scale production of semicarbazones is an important industrial target. Furthermore, while only two green solvents were analyzed, several other green solvents of similar types can be explored.

Synthesis of Semicarbazones: Solutions containing 100%, 90%, 80%, 70%, and 60% ethyl lactate in water were prepared as solvents. This process was repeated for dimethyl isosorbide solutions of concentration 100%, 98%, 96%, 94%, 92%, and 90%. A semicarbazide standard was also prepared by creating a 1 mmol solution in water. For the reaction, 1 mmol of a substituted benzaldehyde was dissolved in 0.3 mL of the solvent, which varied in concentration for each trial. 0.25 mL of the semicarbazide solution was then added to this mixture, and the reaction proceeded in a reaction tube. The mixture was vortexed, and the time to precipitation was recorded. Eventually the reaction tube was placed in a freezer to aid crystallization. The products were filtered using a Hirsch funnel, washed with distilled water, and dried in a vacuum oven for 48 hours. Finally, the dried products were weighed and yields were calculated. The semicarbazide-benzaldehyde solutions in 80% ethyl lactate and 92% dimethyl isosorbide solutions produced the best yields.

Figure 3:
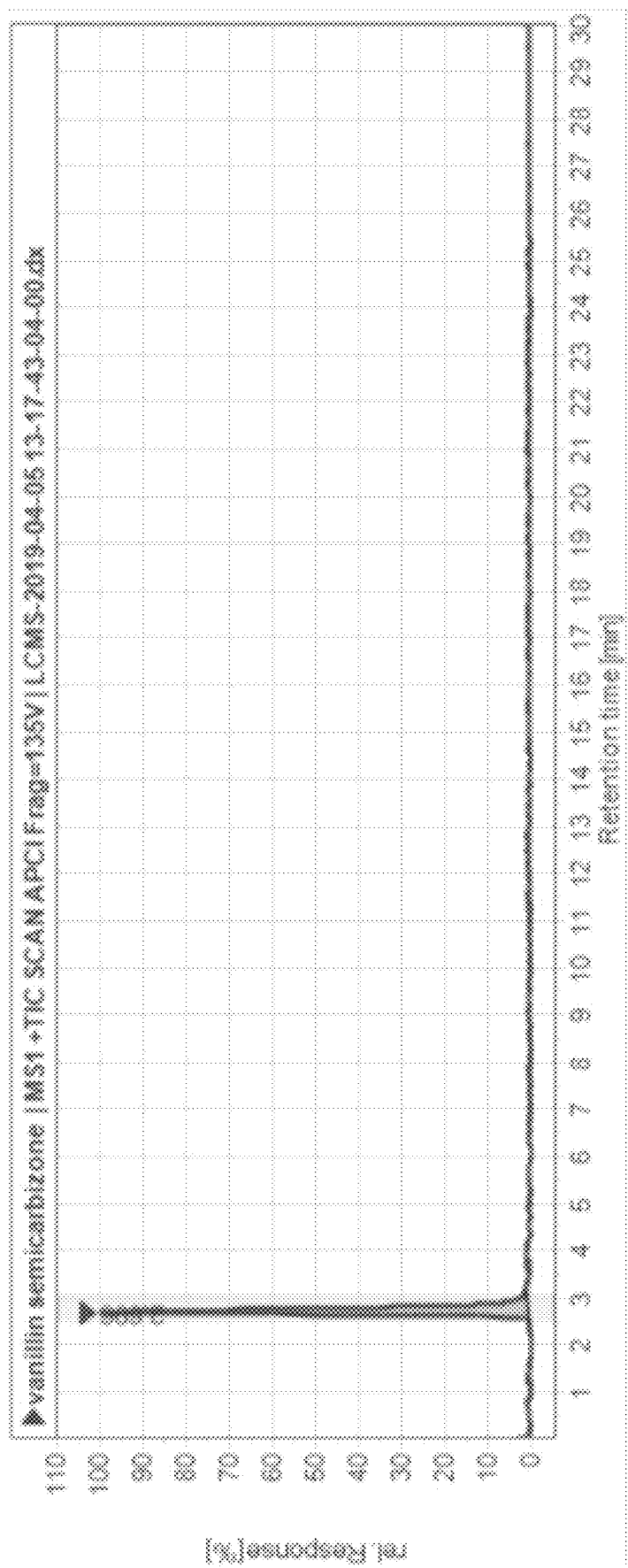
FIG. 3 depicts a liquid chromatogram for vanillin semicarbazone wherein the presence of one peak in the separation indicated product purity.
Figure 4:
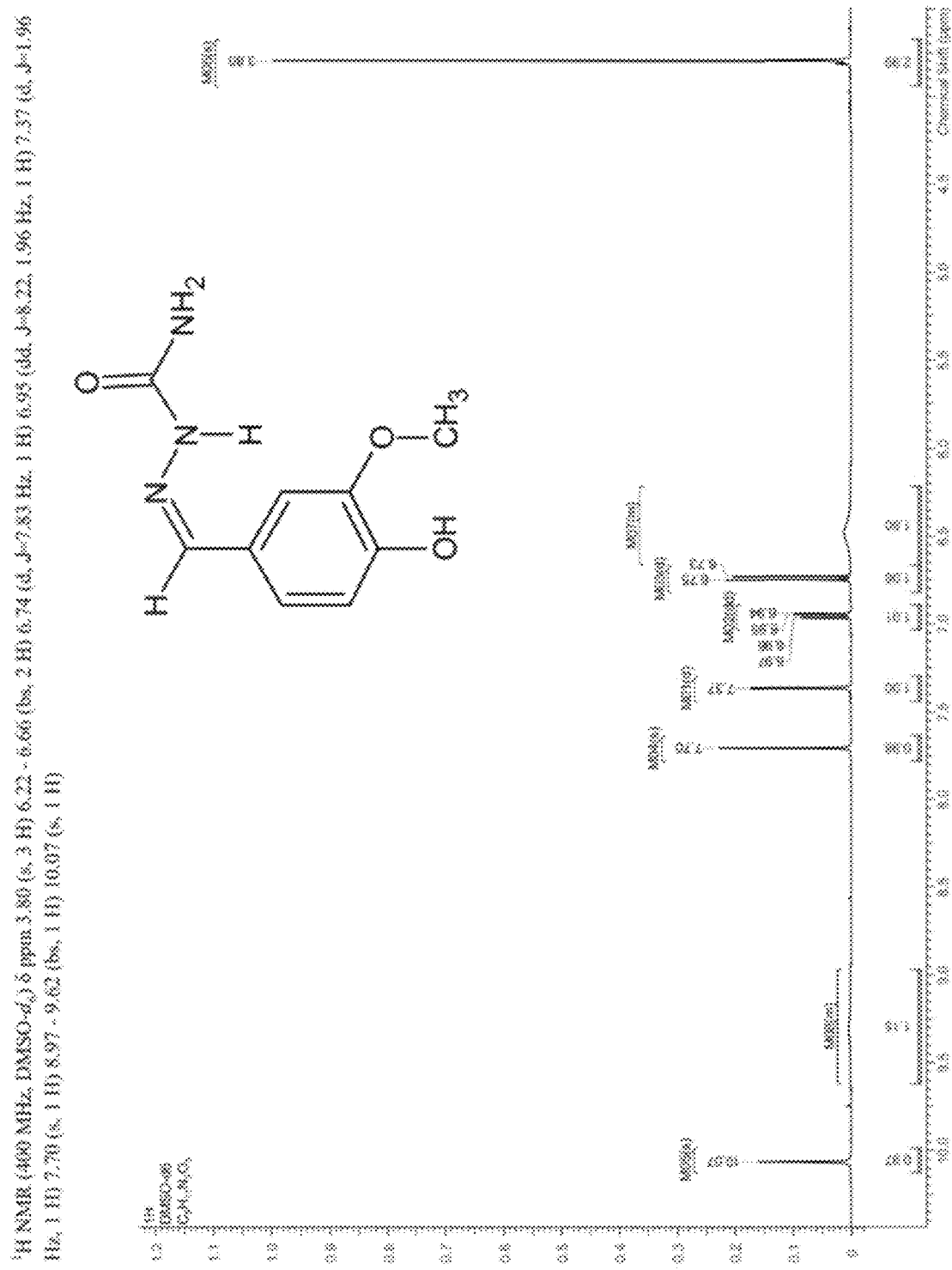
FIG. 4 depicts $^1$H NMR spectrum for vanillin semicarbazone, wherein vanillin semicarbazone was prepared in DMSO and analyzed for structure using a 400 MHz Varian NMR Spectrometer.
Figure 5:
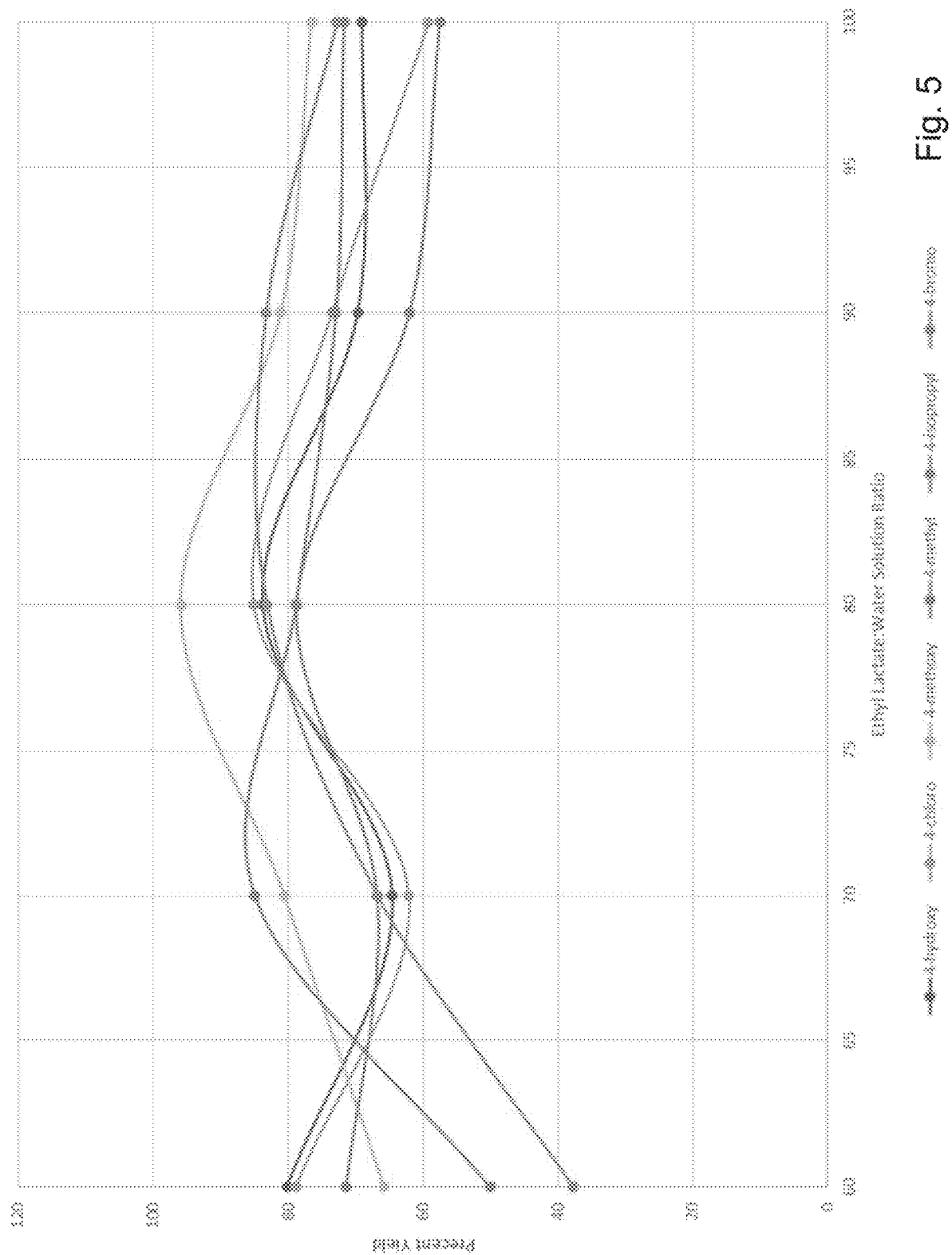
FIG. 5 depicts yields in different ethyl lactate concentrations, wherein peak yields were achieved in 80% mixture.
Figure 6:
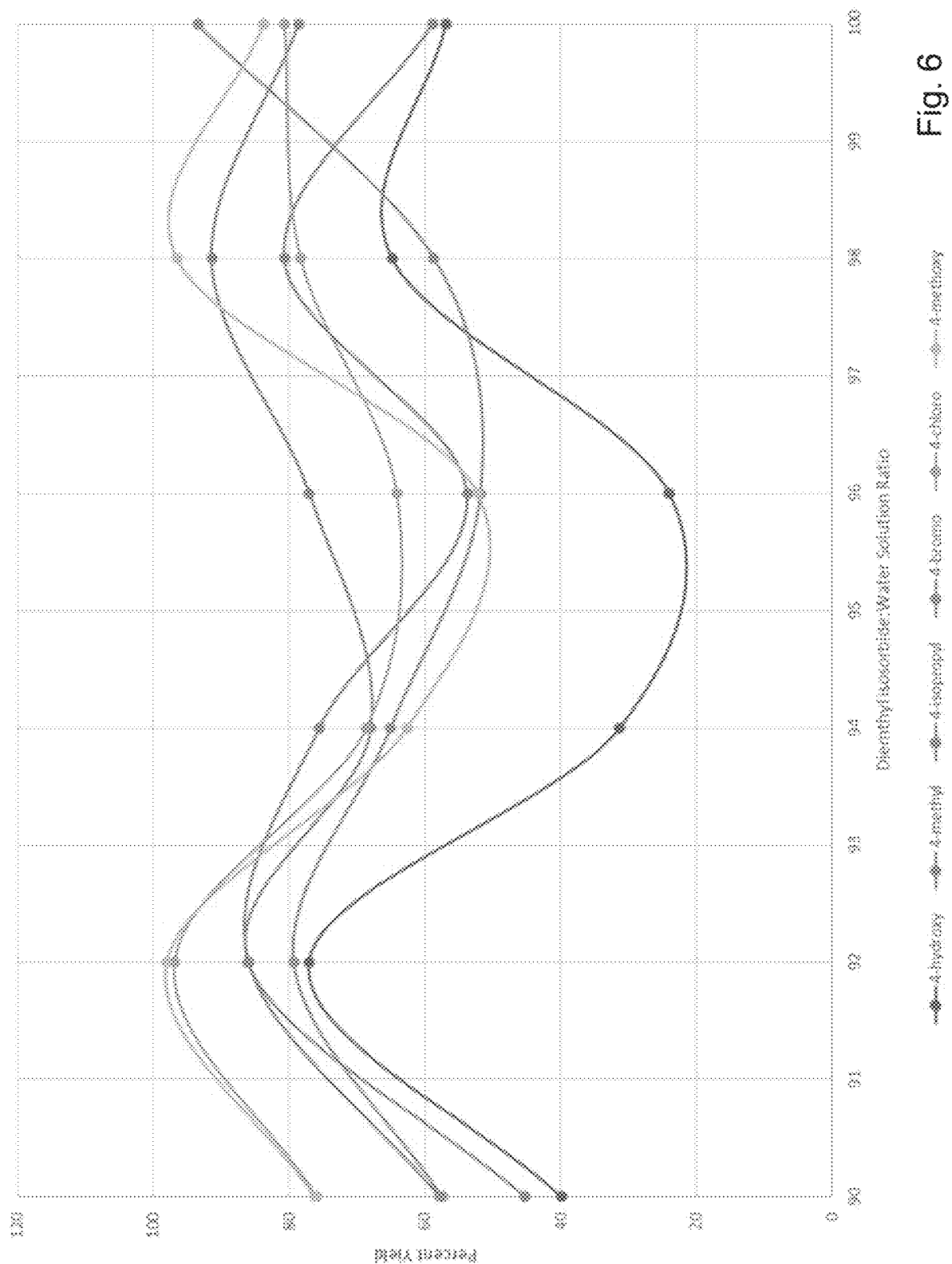
FIG. 6 depicts yields in different dimethyl isosorbide concentrations, wherein peak yields were achieved in 92% mixture.
Figure 7:
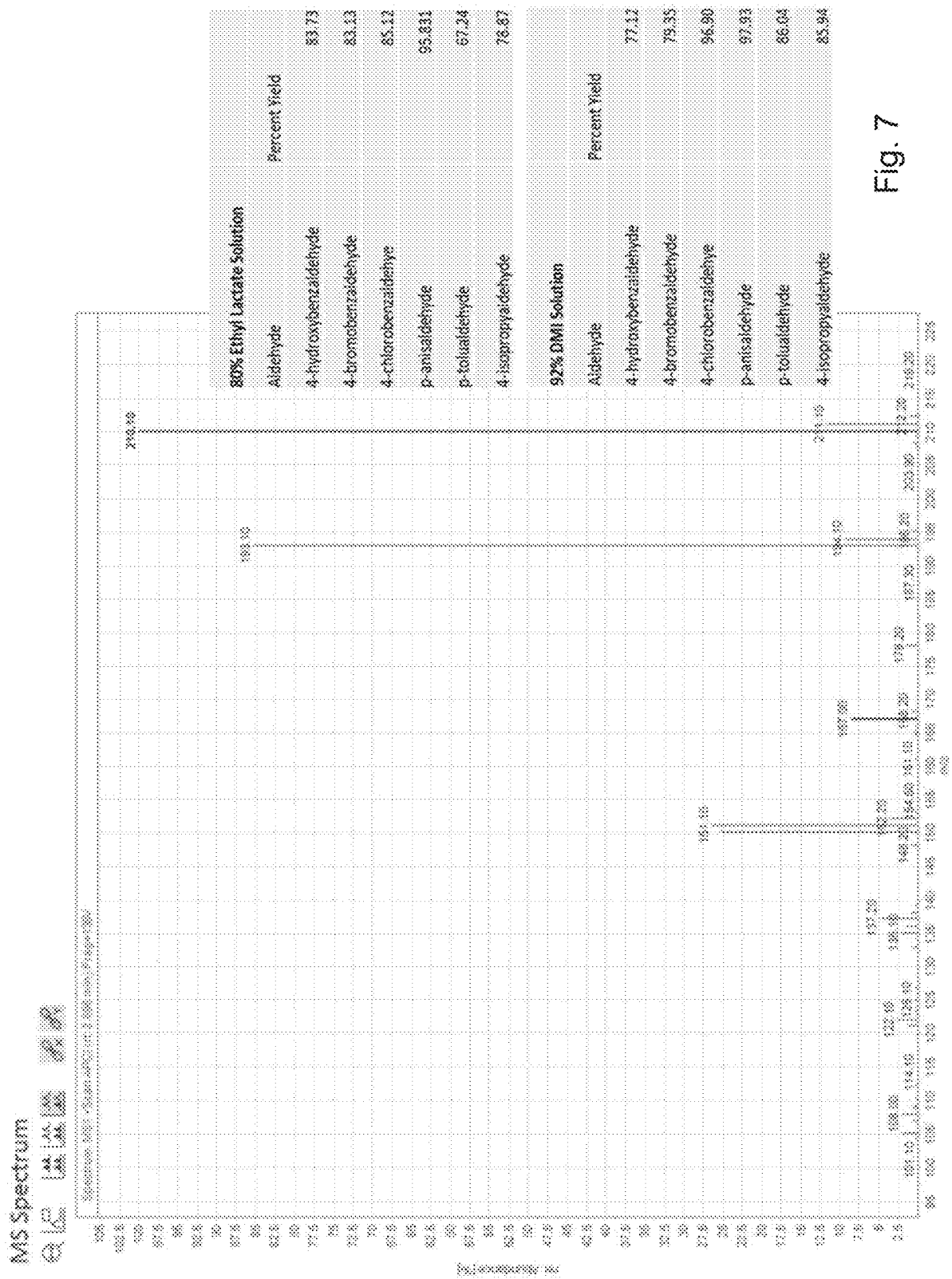
FIG. 7 depicts mass spectrum for vanillin semicarbazone, wherein the peak at m/z=210 corresponds to the M+ peak, with the peak at m/z=193 representing the fragmentation for the loss of the hydroxy group.

LC-MS: Semicarbazones produced in 80% ethyl lactate and 92% dimethyl isosorbide were prepped for LC-MS analysis using 60% acetonitrile as a solvent, and analyzed using a Agilent 1260 Infinity™ spectrometer. Liquid chromatography tested for purity and mass spectrometry confirmed the completion of the reaction. Vanillin semicarbazone is shown in FIGS. 3 and 7.

Discussion & Conclusions

The results of the syntheses indicate that the best yields were in the presence of an 80:20 ethyl lactate:water mixture and a 92:8 dimethyl isosorbide:water mixture. The results of the NMR analysis show that the products made fit the expected structure. In addition, the LC-MS analyses indicated a high degree of purity, where only one product peak appeared with only small traces of starting material detected. The mass spectrum also proved the structure of the compounds by providing the expected molecular ion peak and fragmentation pattern. It can therefore be concluded that the proposed synthesis works in two novel green solvents, the products of which are high yielding and highly pure. Future study will investigate the scaling up of this reaction for industrial use, as well as the use of other green solvents.

Additional Examples

Example 9

Lactic whey was obtained from a regional dairy company headquartered in Syracuse, N.Y. It was stored in a refrigerator until use, without any special treatment prior to use. The pH of the lactic whey was determined to be between 5-6. A variety of reactions were performed using mixtures of ethyl lactate (a biodegradable and bio-renewable, green solvent). As a beginning point, a solution of 80% ethyl lactate and 20% lactic whey was made and used as the solvent mixture for the reactions. All reactions were carried out at either room temperature or 50 degrees Celsius. The following functional groups were created in these reaction mixtures: imines, oximes, semicarbazones, 1,4-quinoxalines, and 1,4-quinoxalin-2-ones. 4-thiazolidinones were also made using a lactic whey in accordance with the present disclosure. The general procedures are as follows: Imines: Imines were created from aryl amines and aryl aldehydes. For solid aryl amines or solid aryl aldehydes, the starting compounds were dissolved in the solvent first, then combined to initiate the reaction. For solid aryl amines and liquid aryl aldehydes, the aryl amine was dissolved in the solvent first, then the liquid aryl aldehyde was added to initiate the reaction. Reactions were generally finished within 10 minutes at room temperature, with some being done within 1 minute. Reaction completion was determined by the formation of a solid product which precipitated from solution until the entire volume of the solution was solid. Products were isolated by vacuum filtration, washed with 80% ethyl lactate in water and pure water, then allowed to dry before further analysis. While several imines were created, only one was used to determine yields and purity and compared to the standard reaction conditions using 80% ethyl lactate with 20% water. Yields for (E)-N-(4-Methoxybenzylidene)-4-methylaniline were 72.6% with lactic whey:ethyl lactate compared to 77.3% for water:ethyl lactate (both at 80% ethyl lactate:20% co-solvent). Purities for this compound were 98.7% for lactic whey:ethyl lactate and 99.3% for water:ethyl lactate, without recrystallization which is a typical purification process when a solid product is produced. The decrease in yield and purity was expected due to the nature of the composition of lactic whey (vide infra).

Oximes: Two oximes were produced. The presence of one oxime product was determined by thin-layer chromatography (TLC). The procedure was modified from the imine recipe as follows: pyridine-2-carboxyaldehyde (a liquid aldehyde) and 50% aqueous hydroxyl amine were added to a solution of 80% ethyl lactate:20% lactic whey. The product oxime is known to be a solid, so it must be soluble in the reaction medium to such an extent that it is not precipitating as normal. Increasing the concentration from 1 M to 2 M may be beneficial. The second oxime produced was made as follows: anisaldehyde was added to 0.5 mL of 80% ethyl lactate:20% lactic whey followed by a 50% aqueous solution of hydroxyl amine. The resulting solution was heated to 35 degrees Celsius for ~30 seconds until the solution become cloudy as a precipitate began to form. The solution was allowed to cool to room temperature to complete crystallization of the product.

Semicarbazones: One semicarbazone was created from a solid aldehyde (vanillin) and semicarbazide hydrochloride as follows. Vanillin was dissolved in 80% ethyl lactate:20% lactic whey and semicarbazone hydrochloride was dissolved in the minimum amount of water. The aqueous solution of semicarbazone hydrochloride was added to the vanillin solution to initiate the reaction. The reaction began to form a precipitate in ~6 minutes and was done in ~60 minutes, a time comparable to the standard 80% ethyl lactate:20% water solvent mixture.

1,4-quinoxalines: One 1,4-quinoxaline was created by reaction of ortho-phenylenediamine with benzil. The ortho-phenylenediamine was dissolved in 80% ethyl lactate:20% lactic whey to produce a green solution. The benzil was dissolved in a 90% ethyl lactate:10% lactic whey solution at 50 degrees Celsius. These two solutions were combined to initiate the reaction and the resulting mixture held at 50 degrees Celsius for 15 minutes until a precipitate began to form and the green color began to discharge, then the reaction was allowed to cool to room temperature to complete the solidification of the product. 1,4-quinoxalin 2-ones: One 1,4-quinoxalin-2-one was produced from ortho-phenylenediamine and ethyl pyruvate. A solution was first created from ortho-phenylenediamine and 80% ethyl lactate:20% lactic whey to form a green solution. To this solution was added ethyl pyruvate. The reaction was complete in less than 60 seconds as seen by the formation of a precipitate.

The foregoing Figures above, FIGS. 1-20 show some of the processing associated according to several embodiments of this disclosure. In this regard, each drawing or block within a flow diagram of the drawings represents a process associated with embodiments of the method described. It should also be noted that in some alternative implementations, the acts noted in the drawings or blocks may occur out of the order noted in the figure or, for example, may in fact be executed substantially concurrently or in the reverse order, depending upon the act involved. Also, one of ordinary skill in the art will recognize that additional blocks that describe the processing may be added.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. "Optional" or "optionally" means that the subsequently described event or circumstance may or may not occur, and that the description includes instances where the event occurs and instances where it does not.

Approximating language, as used herein throughout the specification and claims, may be applied to modify any representation that could permissibly vary without resulting in a change in the basic function to which it is related. Accordingly, a value modified by a term or terms, such as "about," "approximately" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. "Approximately" as applied to a particular value of a range applies to both values, and unless otherwise dependent on the precision of the instrument measuring the value, may indicate +/−10% of the stated value(s).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A method of forming an imine, imine-related or imine-derived compound product, comprising the steps of:
   mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.) to form a mixture, wherein the green solvent comprises an aqueous solution of dimethyl isosorbide or an aqueous solution of ethyl lactate;
   stirring the mixture for a first duration; and
   forming an imine, imine-related or imine-derived compound product.

2. The method of claim 1, wherein the first reactant is one or more of an aldehyde, ketone, or ester.

3. The method of claim 1, wherein the second reactant is further characterized as a nucleophilic/nitrogen-containing reactant.

4. The method of claim 1, wherein the imine-related compound is one or more of oxime, azine, hydrazone, phenylhydrazone, or semicarbazones.

5. The method of claim 1, wherein the first reactant is an ester and the compound product is characterized as quinoxalinone.

6. The method of claim 1, wherein the green solvent comprises an aqueous solution of ethyl lactate over a range of concentration ratios from 60:40 to 100:0, 70:30 to 90:10, or 75:25 to 85:15 of ethyl lactate:water.

7. The method of claim 1, wherein the green solvent further comprises an aqueous solution of ethyl lactate at a concentration ratio of 80:20 ethyl lactate:water.

8. The method of claim 1, wherein the green solvent comprises an aqueous solution of dimethyl isosorbide over a range of concentration ratios from 85:15 to 100:0, 90:10 to 95:5, or 92:8 of dimethyl isosorbide:water.

9. The method of claim 1, wherein the green solvent comprises an aqueous solution of ethyl lactate over a range of concentration ratios from 60:40 to 100:0, 70:30 to 90:10, or 75:25 to 85:15 of ethyl lactate:lactic whey.

10. The method of claim 9, wherein the lactic whey is acidic whey.

11. The method of claim 1, further comprising the steps of:
    mixing the first reactant into solution in the green solvent to form a green solvent aldehyde solution, wherein the first reactant is an aldehyde reactant;
    mixing the second reactant into solution in water to form an aqueous nucleophilic/nitrogen-containing solution, wherein the second reactant is a nucleophilic/nitrogen containing reactant;
    mixing the green solvent aldehyde solution with the aqueous nucleophilic/nitrogen-containing solution;
    stirring the green solvent aldehyde solution together with the aqueous nucleophilic/nitrogen-containing solution; and
    forming an imine, imine-related or imine-derived compound product.

12. The method of claim 1, wherein the first reactant is an aldehyde reactant comprising a substituted benzaldehyde.

13. The method of claim 1, wherein the second reactant is a nucleophilic/nitrogen-containing reactant comprising a semicarbazide hydrochloride.

14. The method of claim 1, wherein the first reactant is an aldehyde reactant and the second reactant is a nucleophilic/nitrogen-containing reactant, and wherein the method comprises: heating the first reactant in an aqueous solution to form a supersaturated green solvent aldehyde solution; and
    mixing the second reactant into the supersaturated green solvent aldehyde solution within zero (0) to thirty (30) seconds after the first reactant is totally dissolved and completely enters solution in the green solvent.

15. A method of forming an imine, imine-related or imine-derived compound product, comprising the steps of:
    mixing a first reactant characterized as a carbonyl-containing compound with a second reactant characterized as a nitrogen-containing reactant in a green solvent at a temperature between negative twenty degrees Celsius (−20° C.) and fifty degrees Celsius (50° C.) to form a mixture, wherein the green solvent comprises an aqueous solution of ethyl lactate and lactic whey;
    stirring the mixture for a first duration; and
    forming an imine, imine-related or imine-derived compound product.

16. The method of claim 15, wherein the lactic whey is acidic whey.

17. The method of claim 15, wherein the green solvent comprises an aqueous solution of ethyl lactate over a range of concentration ratios from 70:30 to 90:10, or 75:25 to 85:15 of ethyl lactate:lactic whey.

18. A solvent solution suitable for forming an imine, imine-related or imine-derived compound, or pharmaceutically acceptable salt thereof, comprising: an aqueous solution of ethyl lactate and lactic whey.

19. The solvent solution of claim 18, wherein the aqueous solution comprises ethyl lactate over a range of concentration ratios from 70:30 to 90:10, or 75:25 to 85:15 of ethyl lactate:lactic whey.

20. The solvent solution of claim 19, wherein the lactic whey is acidic whey or sweet whey.

* * * * *